(12) United States Patent
Nakamura et al.

(10) Patent No.: US 10,229,485 B2
(45) Date of Patent: Mar. 12, 2019

(54) INFORMATION PROCESSING APPARATUS AND INFORMATION PROCESSING METHOD

(71) Applicant: SONY CORPORATION, Tokyo (JP)

(72) Inventors: Yusuke Nakamura, Kanagawa (JP); Toru Igami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/522,920

(22) PCT Filed: Aug. 25, 2015

(86) PCT No.: PCT/JP2015/073900
§ 371 (c)(1),
(2) Date: Apr. 28, 2017

(87) PCT Pub. No.: WO2016/075979
PCT Pub. Date: May 19, 2016

(65) Prior Publication Data
US 2017/0316554 A1    Nov. 2, 2017

(30) Foreign Application Priority Data
Nov. 12, 2014 (JP) .................. 2014-229890

(51) Int. Cl.
*G06K 9/40* (2006.01)
*G06T 5/00* (2006.01)
(Continued)

(52) U.S. Cl.
CPC ................ *G06T 5/009* (2013.01); *A61B 5/00* (2013.01); *A61B 5/0077* (2013.01); *G03B 7/093* (2013.01);
(Continued)

(58) Field of Classification Search
None
See application file for complete search history.

(56) References Cited

U.S. PATENT DOCUMENTS

| 5,541,706 A | 7/1996 | Goto |
| 2006/0023271 A1* | 2/2006 | Boay ................... H04N 1/4005 |
| | | 358/504 |

(Continued)

FOREIGN PATENT DOCUMENTS

| JP | 2007-017623 A | 1/2007 |
| JP | 2007-053481 A | 3/2007 |

(Continued)

OTHER PUBLICATIONS

Extended European Search Report of EP Application No. 15858317.9, dated May 18, 2018, 06 pages of EESR.

*Primary Examiner* — Sean M Conner
(74) *Attorney, Agent, or Firm* — Chip Law Group

(57) ABSTRACT

Provided is an information processing apparatus including: a photographing information acquisition unit configured to acquire an image at a time of photographing photographed by a camera and a temperature of an illumination light source at the time of photographing; and a correction unit configured to correct a brightness of the image at the time of photographing or an exposure time period of the camera on the basis of the temperature of the illumination light source at the time of photographing, the brightness of the image at the time of photographing, and temperature characteristics of the illumination light source, the temperature characteristics having been prepared in advance.

17 Claims, 21 Drawing Sheets

(51) Int. Cl.
  *A61B 5/00* (2006.01)
  *G03B 7/093* (2006.01)
  *G03B 15/05* (2006.01)
  *H04N 5/238* (2006.01)
  *H04N 5/243* (2006.01)
  *H04N 5/225* (2006.01)
  *H04N 5/235* (2006.01)

(52) U.S. Cl.
  CPC ........... G03B 15/05 (2013.01); H04N 5/2256 (2013.01); H04N 5/238 (2013.01); H04N 5/2351 (2013.01); H04N 5/243 (2013.01); *G03B 2215/0567* (2013.01); *G03B 2215/0575* (2013.01)

(56) References Cited

U.S. PATENT DOCUMENTS

| | | | | |
|---|---|---|---|---|
| 2006/0251408 A1* | 11/2006 | Konno | ................. | A61B 5/4547 396/14 |
| 2008/0075448 A1 | 3/2008 | Awazu | | |
| 2010/0220344 A1* | 9/2010 | Tashiro | .............. | H04N 1/40056 358/1.13 |
| 2011/0142365 A1* | 6/2011 | Sakagami | ............ | G02B 21/365 382/274 |
| 2014/0016832 A1* | 1/2014 | Kong | ................... | A61B 5/1171 382/115 |
| 2015/0213619 A1* | 7/2015 | Nakamura | ........... | A61B 5/0077 382/128 |
| 2016/0317041 A1* | 11/2016 | Porges | ................. | A61B 5/7235 |
| 2017/0202445 A1* | 7/2017 | Sakai | ....................... | A61B 1/06 |

FOREIGN PATENT DOCUMENTS

| | | | | |
|---|---|---|---|---|
| JP | 2007-166643 A | | 6/2007 | |
| JP | 2008-118635 A | | 5/2008 | |
| JP | 4482021 B2 | | 6/2010 | |
| JP | 4851283 B2 | | 1/2012 | |
| JP | WO 2014027522 A1 * | | 2/2014 | ........... A61B 5/0077 |
| WO | 2014/103954 A1 | | 7/2014 | |

* cited by examiner

FIG. 19
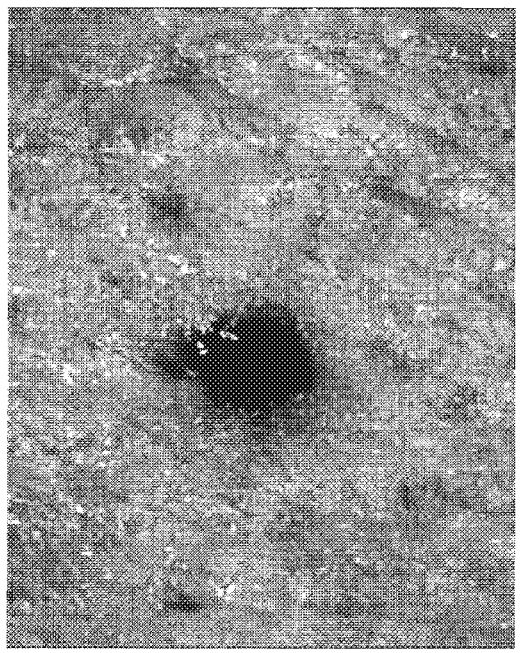
AFTER CORRECTION
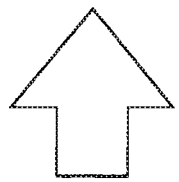
BEFORE CORRECTION

FIG. 22
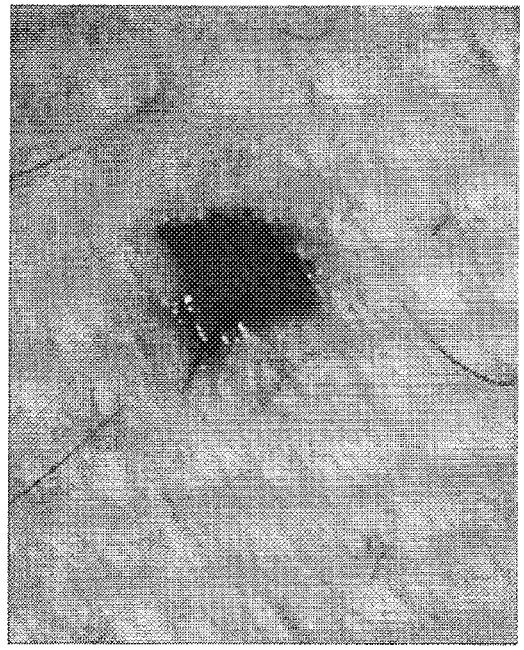
AFTER CORRECTION
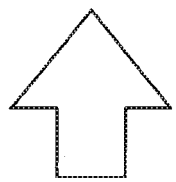
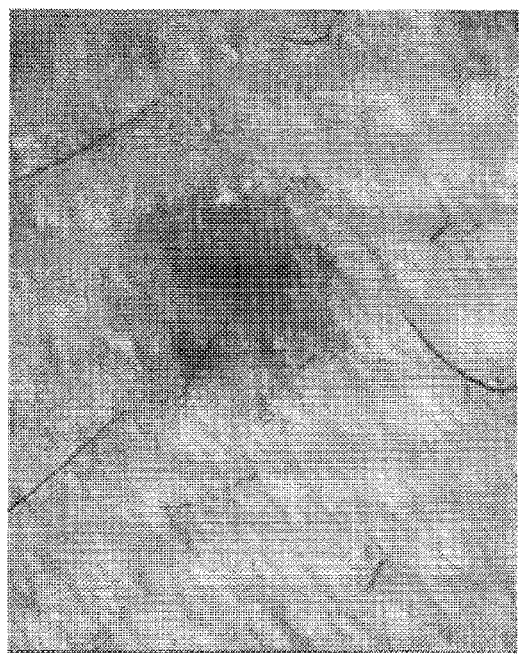
BEFORE CORRECTION

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2015/073900 filed on Aug. 25, 2015, which claims priority benefit of Japanese Patent Application No. JP 2014-229890 filed in the Japan Patent Office on Nov. 12, 2014. Each of the above-referenced applications is hereby incorporated herein by reference in its entirety.

TECHNICAL FIELD

The present invention relates to an information processing apparatus, an information processing method, and a program.

BACKGROUND ART

Luminous intensity (brightness) of an illumination light source such as a light emitting diode (LED) is known to change generally depending on temperature. Therefore, for example, if an image at a time of being irradiated with light emitted from an illumination light source is photographed, the brightness of the image changes depending on temperature. Accordingly, a technology is disclosed including measuring temperature of an illumination light source, and checking the measured temperature against temperature characteristics of the illumination light source, thereby driving and controlling the illumination light source such that the luminous intensity of the illumination light source becomes optimum (for example, see Patent Literature 1).

CITATION LIST

Patent Literature

Patent Literature 1: JP 2008-118635A

DISCLOSURE OF INVENTION

Technical Problem

However, it is desirable to provide a technology including adjusting the brightness of the photographed image with a technique that does not include driving and controlling the illumination light source.

Solution to Problem

According to the present disclosure, there is provided an information processing apparatus including: a photographing information acquisition unit configured to acquire an image at a time of photographing photographed by a camera and a temperature of an illumination light source at the time of photographing; and a correction unit configured to correct a brightness of the image at the time of photographing or an exposure time period of the camera on the basis of the temperature of the illumination light source at the time of photographing, the brightness of the image at the time of photographing, and temperature characteristics of the illumination light source, the temperature characteristics having been prepared in advance.

According to the present disclosure, there is provided an information processing method including: acquiring an image at a time of photographing photographed by a camera and a temperature of an illumination light source at the time of photographing; and correcting, by a processor, a brightness of the image at the time of photographing or an exposure time period of the camera on the basis of the temperature of the illumination light source at the time of photographing, the brightness of the image at the time of photographing, and temperature characteristics of the illumination light source, the temperature characteristics having been prepared in advance.

According to the present disclosure, there is provided a program for causing a computer to function as an information processing apparatus including: a photographing information acquisition unit configured to acquire an image at a time of photographing photographed by a camera and a temperature of an illumination light source at the time of photographing; and a correction unit configured to correct a brightness of the image at the time of photographing or an exposure time period of the camera on the basis of the temperature of the illumination light source at the time of photographing, the brightness of the image at the time of photographing, and temperature characteristics of the illumination light source, the temperature characteristics having been prepared in advance.

Advantageous Effects of Invention

According to the present disclosure described above, the brightness of the photographed image can be adjusted with a technique that does not include driving and controlling the illumination light source. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 19 is a diagram showing an example of images before and after brightness correction according to the fifth embodiment of the present disclosure.

FIG. 22 is a diagram showing an example of images before and after brightness correction according to the sixth embodiment of the present disclosure.

MODE(S) FOR CARRYING OUT THE INVENTION

Figure 1:
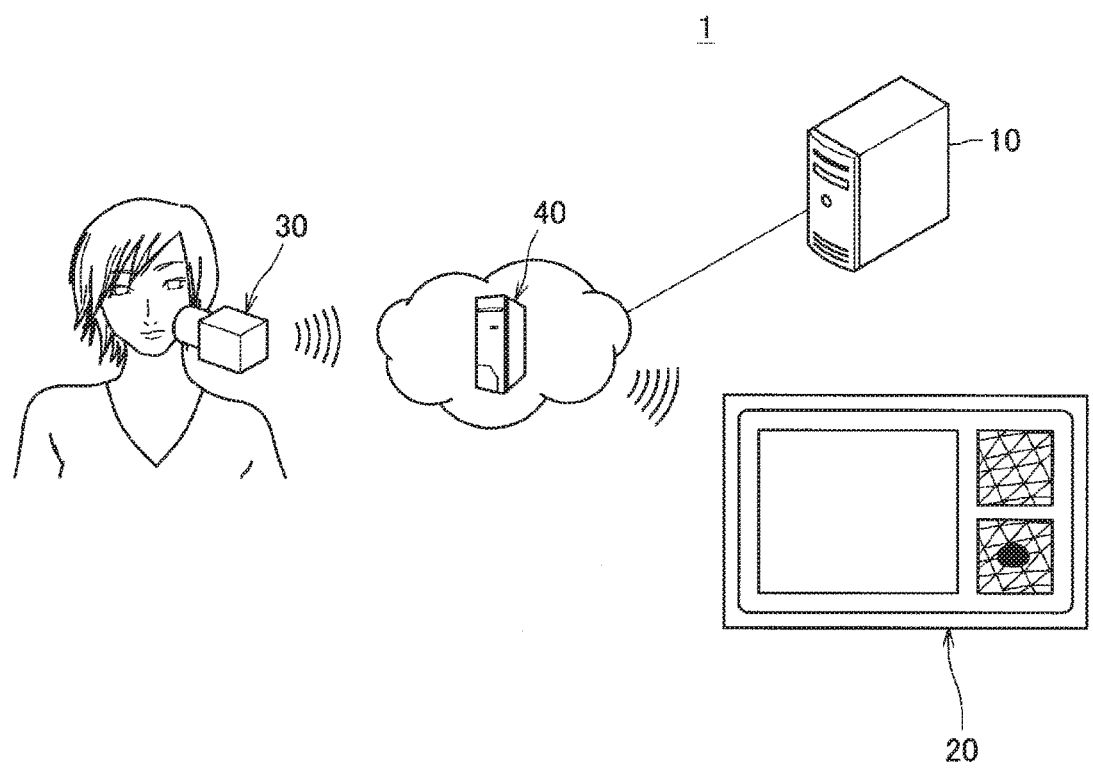
FIG. 1 is a diagram showing a configuration example of a skin analysis system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference signs, and repeated explanation of these structural elements is omitted.

Note that, in this description and the drawings, structural elements that have substantially the same function and structure are sometimes distinguished from each other using different alphabets or numerals after the same reference sign. However, when there is no need in particular to distinguish structural elements that have substantially the same function and structure, the same reference sign alone is attached.

Note that the description will be given in the following order.

0. Overview of embodiment
1. Description of first embodiment
2. Description of second embodiment
3. Description of third embodiment
4. Description of fourth embodiment
5. Description of fifth embodiment
6. Description of sixth embodiment
7. Hardware configuration example of information processing apparatus
8. Conclusion

0. OVERVIEW OF EMBODIMENT

First, an overview of an embodiment of the present disclosure will be described. FIG. 1 is a diagram showing a configuration example of a skin analysis system according to an embodiment of the present disclosure. As shown in FIG. 1, a skin analysis system 1 according to an embodiment of the present disclosure includes a server 10, an information processing terminal 20, and a camera 30. The information processing terminal 20 may be a personal computer (PC), a smartphone, a mobile phone, a tablet PC, a personal digital assistant (PDA), an HMD, or the like. Further, as shown in FIG. 1, the server 10, the information processing terminal 20, and the camera 30 may be mutually communicable with each other via a relay device 40. For example, the relay device 40 may be a Wi-fi (registered trademark) router or the like.

Figure 2:
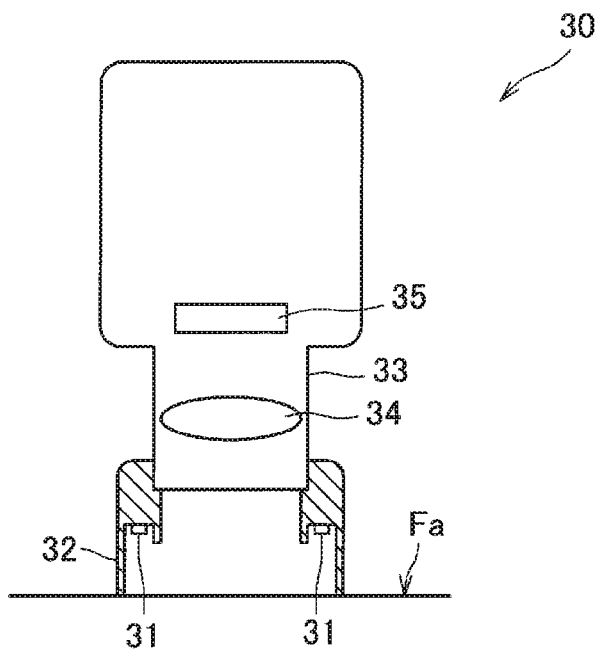
FIG. 2 is a diagram showing a configuration example of a camera.

Here, a configuration example of the camera 30 will be described briefly. FIG. 2 is a diagram showing the configuration example of the camera 30. As shown in FIG. 2, the camera 30 includes an illumination unit 31, a tube 32, a housing 33, a lens 34, and an image sensor 35. The lens 34 and the image sensor 35 are provided inside the housing 33. Further, the illumination unit 31 is provided inside the tube 32.

In the example shown in FIG. 2, the light emitted from the illumination unit 31 reaches a skin surface Fa. Further, the light reflected on the skin surface Fa passes through the lens 34 and reaches the image sensor 35. In this case, in the case where the tube 32 is in contact with the skin surface Fa, the possibility that the light emitted from the illumination unit 31 may leak out of the camera 30 can be reduced, and the possibility that the light which comes inside the camera 30 may reach the image sensor 35 can also be reduced.

A photographed image taken by the image sensor 35 is transmitted to the server 10, and the server 10 may perform skin analysis processing on the photographed image. Further, a skin analysis result obtained by the skin analysis processing is transmitted to the information processing terminal 20, and the information processing terminal 20 may give feedback of the skin analysis result to a user. Note that, although an example in which the skin analysis processing is performed by the server 10 will be mainly described in the embodiment of the present disclosure, the skin analysis processing may also be performed by the information processing terminal 20.

Figure 3:
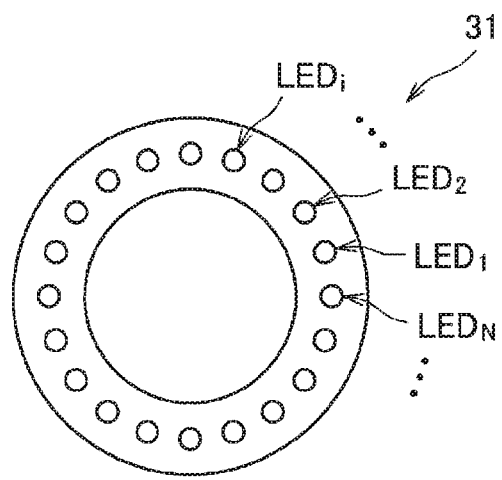
FIG. 3 is a diagram showing a configuration example of an illumination unit.

Subsequently, a configuration example of the illumination unit 31 will be described. FIG. 3 is a diagram showing the configuration example of the illumination unit 31. For example, the illumination unit 31 may include a plurality of illumination light sources. In the example shown in FIG. 3, although the illumination unit 31 includes $LED_1$, $LED_2$, $LED_i$, . . . , $LED_N$ as the plurality of illumination light sources, the type of the illumination light sources is not limited to the light emitting diode (LED). In this way, in the case where the illumination unit 31 includes the plurality of illumination light sources, the plurality of illumination light sources can emit light beams which have different photographing conditions (for example, wavelengths and exposure time periods) from each other.

In the embodiments of the present disclosure, assumed is a scene in which the user attempts to photograph a skin region using the camera 30. In such a scene, since a luminous intensity of an illumination light source of the camera 30 may change depending on temperature, when an image at a time of being irradiated with light emitted from the illumination light source is photographed by the image sensor 35, the brightness of the image changes depending on temperature. If the illumination light source is driven and controlled on the basis of the temperature of the illumination light source, it takes time to stabilize an electric current. Accordingly, the skin analysis system 1 according to an embodiment of the present disclosure adjusts the brightness of the image with a technique that does not include driving and controlling the illumination light source.

Heretofore, the overview of the embodiment of the present disclosure has been described.

1. DESCRIPTION OF FIRST EMBODIMENT

Figure 4:
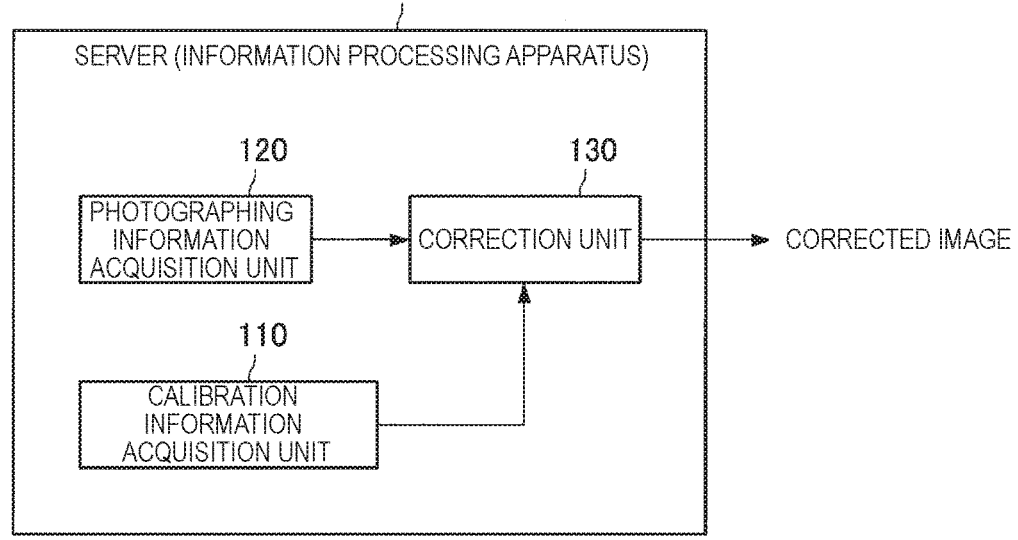
FIG. 4 is a block diagram showing a functional configuration example of a server according to a first embodiment of the present disclosure.

Subsequently, a first embodiment of the present disclosure will be described. First, a functional configuration example of a server (information processing apparatus) 10A according to the first embodiment of the present disclosure will be described. FIG. 4 is a block diagram showing a functional configuration example of the server 10A according to the first embodiment of the present disclosure. As shown in FIG. 4, the server 10A includes a calibration information acquisition unit 110, a photographing information acquisition unit 120, and a correction unit 130. First, functions of the calibration information acquisition unit 110 will be described.

Figure 5:
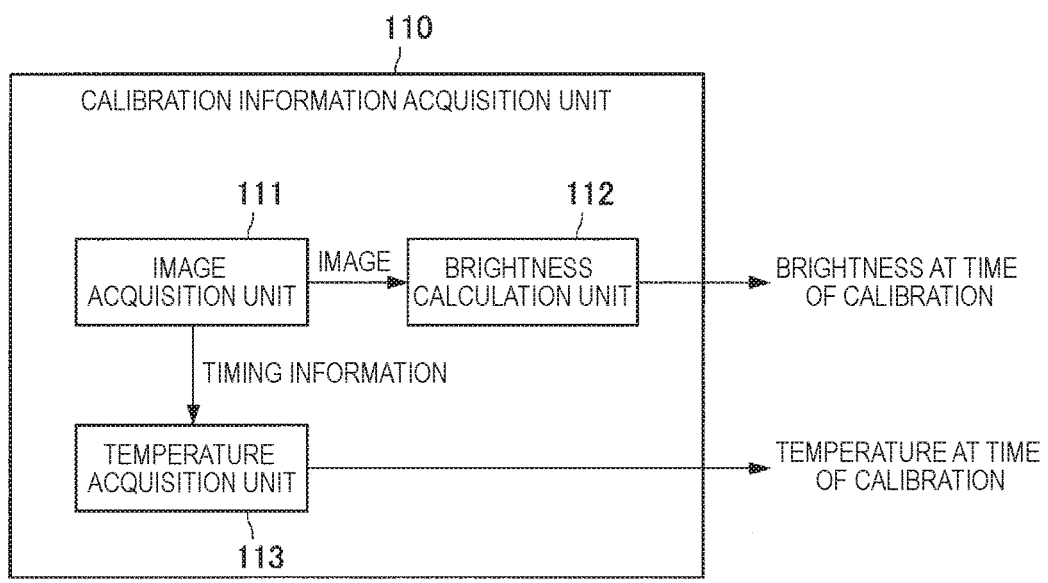
FIG. 5 is a diagram showing a functional configuration example of a calibration information acquisition unit.

FIG. 5 is a diagram showing a functional configuration example of the calibration information acquisition unit 110. As shown in FIG. 5, the calibration information acquisition unit 110 includes an image acquisition unit 111, a brightness calculation unit 112, and a temperature acquisition unit 113. First, the camera 30 photographs a reference material while switching illumination light sources at a time of calibration. Here, as the reference material, it is desirable to use a diffuse reflection standard or the like which has the same reflectance with respect to light having a wavelength of each illumination light source.

Here, let us assume the case where the camera 30 performs switching among the respective illumination light sources (LED) of white light, red light, near-infrared light, and green light, photographs images under the respective illumination light sources (LED's), and provides the image acquisition unit 111 with four images in total. In this case, the images with which the image acquisition unit 111 is provided are represented by $pI_W$, $pI_R$, $pI_{IR}$, and $pI_G$, respectively. The image acquisition unit 111 acquires the images $pI_W$, $pI_R$, $pI_{IR}$, and $pI_G$ at the time of calibration from the camera 30 in this way. Note that the types of the illumination light sources are not limited to the four types. For example, a new LED may be added as a new illumination light source in addition to the four illumination light sources, or unnecessary illumination light source(s) among the four illumination light sources may be deleted.

The brightness calculation unit 112 calculates the respective brightnesses of the images $pI_W$, $pI_R$, $pI_{IR}$, and $pI_G$ at the time of calibration acquired by the image acquisition unit 111. Here, the brightness calculation unit 112 does not necessarily change the method of calculating the brightness for each illumination light source, but may also change the method of calculating the brightness for each illumination light source, as will be described below.

For example, in the case where the illumination light source is a white light source, the brightness calculation unit 112 may use a luminance as the brightness of the image. On the other hand, in the case where the illumination light source is a red light source, since a signal of a red channel of RGB is dominant, the brightness calculation unit 112 desirably uses a value of the red channel signal as the brightness of the image. In the same manner, in the case where the illumination light source is a near-infrared light source, the brightness calculation unit 112 desirably uses a value of the red channel signal as the brightness of the image, and in the case where the illumination light source is a green light source, the brightness calculation unit 112 desirably uses a value of a green channel signal as the brightness of the image.

Here, the brightness of the image may indicate an average value of the brightness of the entire image. For example, the brightness calculation unit 112 may calculate the respective average values of the entire images of the brightnesses of the images $pI_W$, $pI_R$, $pI_{IR}$, and $pI_G$ at the time of calibration. Hereinafter, the average values of the entire images of the brightnesses of the images $pI_W$, $pI_R$, $pI_{IR}$, and $pI_G$ at the time of calibration are represented by $pB_W$, $pB_R$, $pB_{IR}$, and $pB_G$, respectively.

The temperature acquisition unit 113 acquires the temperatures of the illumination light sources at the time of calibration. For example, the temperature acquisition unit 113 acquires, from a thermistor (temperature measuring instrument), the temperatures of the illumination light sources measured by the thermistor or the like at a timing at which the image acquisition unit 111 acquires the images at the time of calibration. The thermistor may be provided at a position at which the temperatures of the illumination light sources can be substantially measured (may be provided near the illumination light sources), and may be provided inside the camera 30. In this case, the temperatures of the illumination light sources acquired by the temperature acquisition unit 113 are represented by $pT_W$, $pT_R$, $pT_{IR}$, and $pT_G$, respectively.

Figure 6:
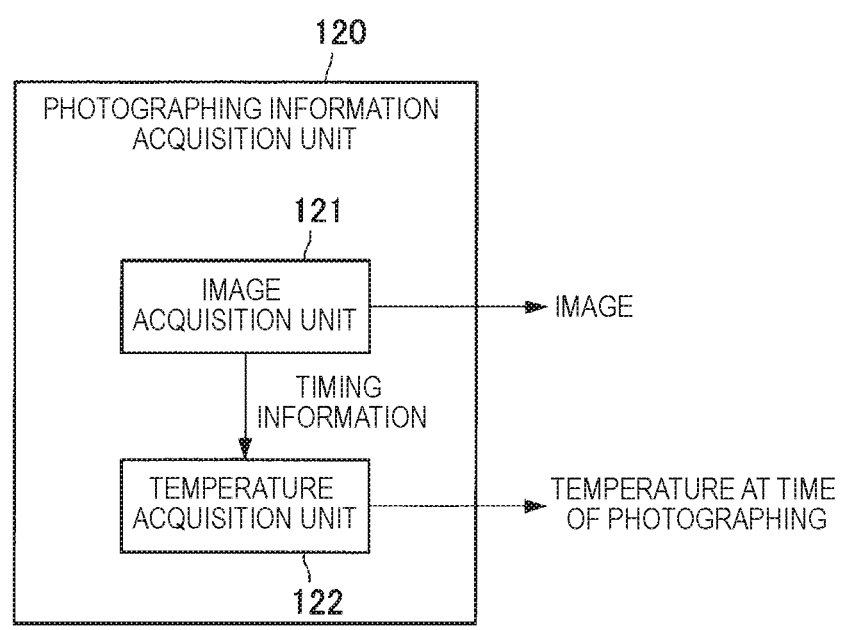
FIG. 6 is a diagram showing a functional configuration example of a photographing information acquisition unit.

FIG. 6 is a diagram showing a functional configuration example of the photographing information acquisition unit 120. As shown in FIG. 6, the photographing information acquisition unit 120 includes an image acquisition unit 121 and a temperature acquisition unit 122. First, the camera 30 photographs a subject such as skin while switching illumination light sources at a time of photographing.

Here, let us assume the case where the camera 30 performs switching among the respective illumination light sources (LED) of white light, red light, near-infrared, and green light, photographs images under the respective illumination light sources (LED's), and provides the image acquisition unit 121 with four images in total. In this case, the images with which the image acquisition unit 121 is provided are represented by $cI_W$, $cI_R$, $cI_{IR}$, and $cI_G$, respectively. The image acquisition unit 121 acquires the images $cI_W$, $cI_R$, $cI_{IR}$, and $cI_G$ at the time of photographing from the camera 30 in this way.

The temperature acquisition unit 122 acquires the temperatures of the illumination light sources at the time of photographing. For example, the temperature acquisition unit 122 acquires, from a thermistor, the temperatures of the illumination light sources measured by the thermistor or the like at a timing at which the image acquisition unit 121 acquires the images at the time of photographing. In this case, the temperatures of the illumination light sources acquired by the temperature acquisition unit 122 are represented by $cT_W$, $cT_R$, $cT_{IR}$, and $cT_G$, respectively.

Figure 7:
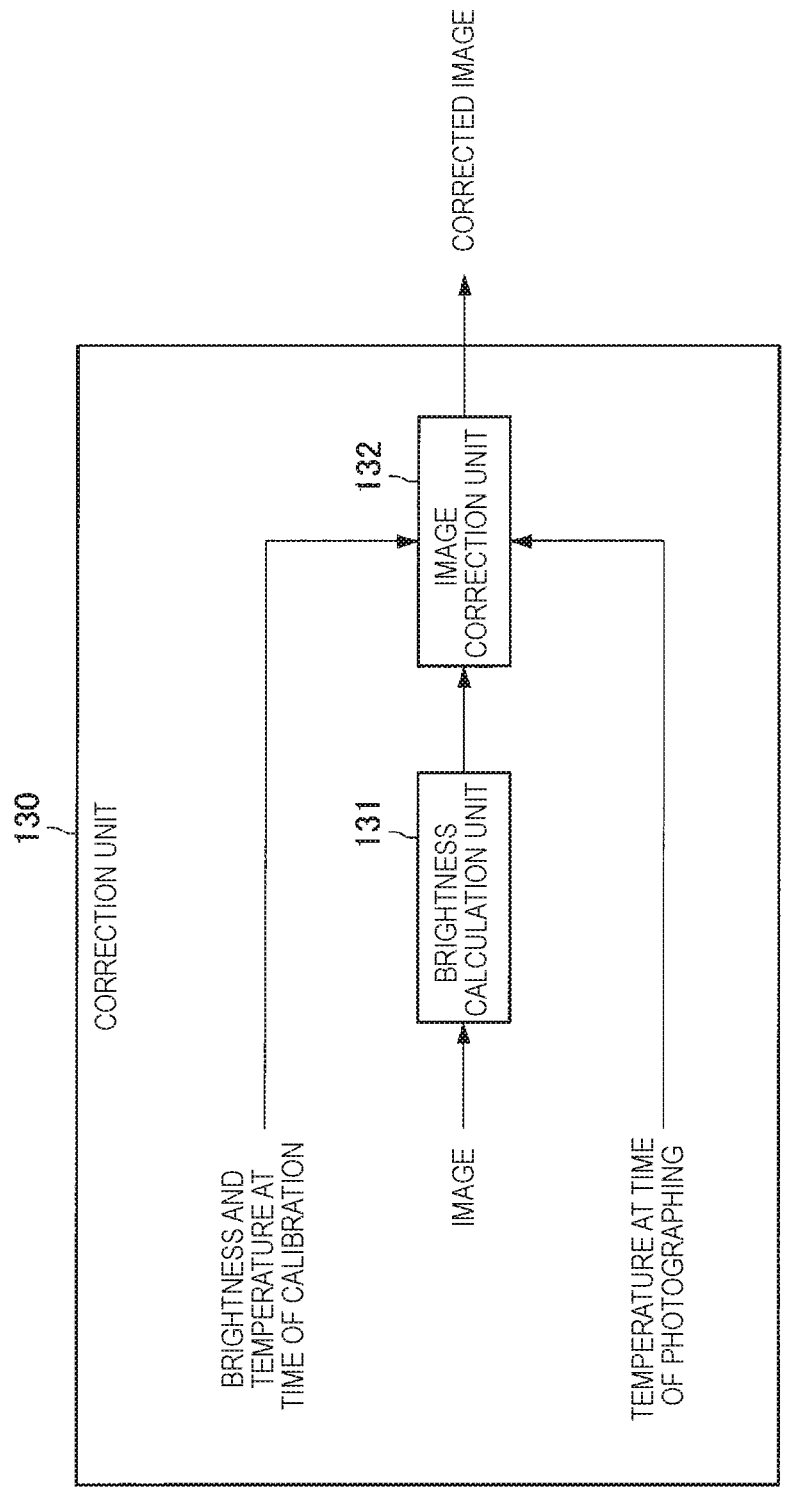
FIG. 7 is a diagram showing a functional configuration example of a correction unit.

FIG. 7 is a diagram showing a functional configuration example of the correction unit 130. As shown in FIG. 7, the correction unit 130 includes a brightness calculation unit 131 and an image correction unit 132. The brightness calculation unit 131 calculates the respective brightness images of the images $cI_W$, $cI_R$, $cI_{IR}$, and $cI_G$ at the time of photographing acquired by the image acquisition unit 121 included in the photographing information acquisition unit 120. Here, the brightness calculation unit 131 does not necessarily change the method of calculating the brightness for each illumination light source, but may also change the method of calculating the brightness for each illumination light source, as will be described below.

For example, in the case where the illumination light source is a white light source, the brightness calculation unit 131 may use a luminance as the brightness of the image. On the other hand, in the case where the illumination light source is a red light source, since a signal of a red channel of RGB is dominant, the brightness calculation unit 131 desirably uses a value of the red channel signal as the brightness of the image. In the same manner, in the case where the illumination light source is a near-infrared light source, the brightness calculation unit 131 desirably uses a value of the red channel signal as the brightness of the image, and in the case where the illumination light source is a green light source, the brightness calculation unit 131 desirably uses a value of a green channel signal as the brightness of the image.

Here, the brightness of the image may indicate an average value of the brightness of the entire image. For example, the brightness calculation unit 131 may calculate the respective average values of the entire images of the brightnesses of the images $cI_W$, $cI_R$, $cI_{IR}$, and $cI_G$ at the time of photographing. Hereinafter, the average values of the entire images of the brightnesses of the images $cI_W$, $cI_R$, $cI_{IR}$, and $cI_G$ at the time of photographing are represented by $cIB_W$, $cIB_R$, $cIB_{IR}$, and $cIB_G$, respectively.

The image correction unit 132 corrects brightnesses of the images at the time of photographing on the basis of the temperatures of the illumination light sources at the time of photographing, the brightnesses of the images at the time of photographing, and temperature characteristics of the illumination light sources, the temperature characteristics having been prepared in advance. In this case, the image correction unit 132 may also use the information at the time of calibration. That is, the image correction unit 132 may correct the brightnesses of the images at the time of photographing on the basis of the temperatures of the illumination light sources at the time of photographing, the temperatures of the illumination light sources at the time of calibration, the brightnesses of the images at the time of photographing, the brightnesses of the images at the time of calibration, and the temperature characteristics of the illumination light sources.

Figure 8:
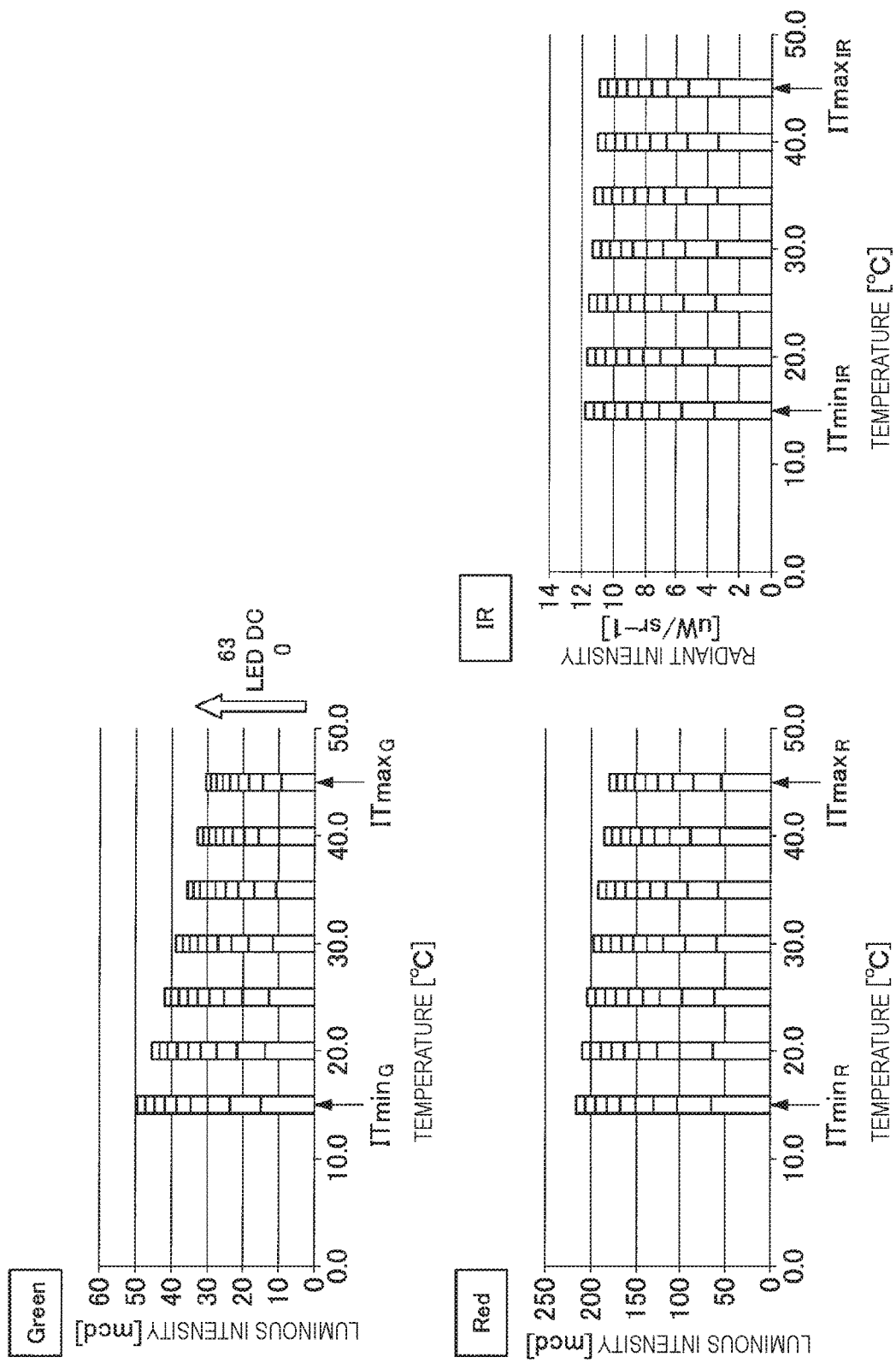
FIG. 8 is a diagram showing an example of temperature characteristics of each illumination light source (LED).

Here, the temperature characteristics will be described. FIG. 8 is a diagram showing an example of the temperature characteristics of each illumination light source (LED). FIG. 8 shows a luminous intensity or a radiant intensity corresponding to each temperature for each of the green light source, the red light source, and the near-infrared light source. In this manner, the temperature characteristics of each illumination light source (LED) may correspond to the luminous intensity or the radiant intensity of each illumination light source (LED) corresponding to each temperature. Further, in the example shown in FIG. 8, ITmin and ITmax represent a lower limit and an upper limit, respectively, of the temperature of each of the illumination light sources at the time of measuring the temperature characteristics.

Moreover, as shown in FIG. 8, the luminous intensity or the radiant intensity of the illumination light source generally decreases as the temperature increases. However, as shown in FIG. 8, the rate at which the luminous intensity or the radiant intensity of the illumination light source decreases with the increase in temperature generally changes depending on a value of a driving current (DC value) of the illumination light source (LED). Accordingly, a slope of the luminous intensity (or the radiant intensity) with respect to the temperature can be approximated by polynomials using the DC value of the illumination light source (LED) in accordance with the following formula (1).

[Math. 1]

$$\text{temp\_intensity\_slope}_i = \sum_n \text{coef}_i^n \cdot (\text{led\_dc}_i)^n \qquad (1)$$

In formula (1), the subscript i represents a type of the illumination light source. The subscript i that appears in the following formulae may also be interpreted as the same. Next, the slope of the luminous intensity (or the radiant intensity) of the illumination light source (LED) with respect to the DC value can be calculated in accordance with the following formula (2).

[Math. 2]

$$dc\_\text{intensity\_slope} = \text{init\_intensity}_i - (cT_i - \text{init\_temp}_i) \cdot \text{delta\_intensity}_i \qquad (2)$$

In formula (2), init_temp represents the temperature (initial temperature) of the illumination light source at the time of calibration, init_intensity represents the slope of the luminous intensity with respect to the DC value of the illumination light source at the initial temperature, and delta_intensity represents an amount of change of the slope of the luminous intensity with respect to the DC value on a per-degree basis. Then, with respect to any DC value, the luminous intensity or the radiant intensity of the illumination light source (LED) may be calculated in accordance with the following formula (3).

[Math. 3]

$$\text{intensity}_i = dc\_\text{intensity\_slope}_i \cdot \text{led\_dc}_i \qquad (3)$$

To formulate this relationship, the brightness at the position (x,y) of the image $nI_i$ after correction may be calculated in accordance with the following formula (4). That is, the image correction unit 132 can correct the brightnesses of the images at the time of photographing on the basis of the following formula (4).

[Math. 4]

$$nI_i(x,y) = cIB_i(x, y) - \text{temp\_intensity\_slope}_i \cdot \text{delta\_temp}_i \cdot pB_i / (\text{intensity}_i \cdot \text{led\_num}_i) \qquad (4)$$

In formula (4), temp_intensity_slope represents the slope of the luminous intensity (or the radiant intensity) of the illumination light source with respect to the temperature of the illumination light source, delta_temp represents a difference between the temperature of the illumination light source at the time of photographing and the temperature of the illumination light source at the time of calibration, intensity represents an average value of the DC value of the illumination light source, and led_num represents the number of illumination light sources that is being equipped.

As described above, according to the first embodiment of the present disclosure, the brightness of the image can be adjusted with a technique that does not include driving and controlling the illumination light source. Accordingly, the time taken to stabilize an electric current is reduced as compared to the technology including driving and controlling the illumination light source on the basis of the temperature of the illumination light source.

Figure 9:
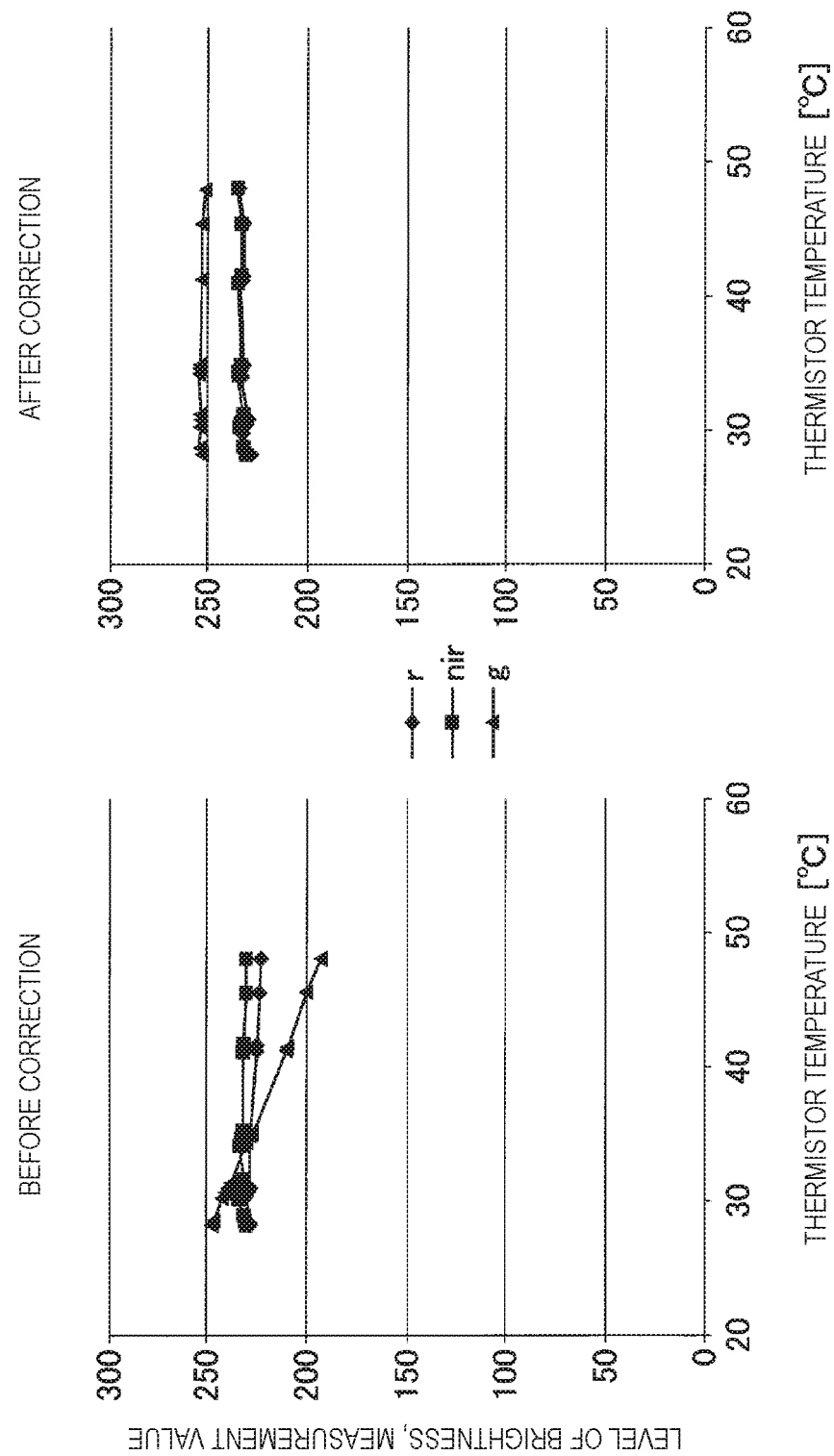
FIG. 9 is a diagram showing an example of a relationship between a temperature (thermistor temperature) of each illumination light source and a brightness of each image before and after brightness correction on an image according to the first embodiment of the present disclosure.

Subsequently, with reference to FIG. 9, the effects achieved by the first embodiment of the present disclosure will be described. FIG. 9 is a diagram showing an example of a relationship between a temperature (thermistor temperature) of each illumination light source and a brightness of each image before and after brightness correction on an image according to the first embodiment of the present disclosure. In the figure, "r" represents the case where the red light source is used as the type of the illumination light source, "nir" represents the case where the near-infrared light source is used as the type of the illumination light source, and "g" represents the case where the green light source is used as the type of the illumination light source.

In the example shown in FIG. 9, "before correction" shows an example of a relationship between the thermistor temperature at the time of photographing the same target object while changing the temperature of each illumination light source and the brightness of each image before correction. On the other hand, "after correction" shows an example of a relationship between the thermistor temperature at the time of photographing the same target object while changing the temperature and the brightness of each image after correction. As shown in FIG. 9, before brightness correction on the image, the brightness of the image decreases with increase in temperature, however, after brightness correction on the image, the decrease in brightness of the image can be suppressed independent of the temperature.

Heretofore, the first embodiment of the present disclosure has been described.

2. DESCRIPTION OF SECOND EMBODIMENT

Subsequently, a second embodiment of the present disclosure will be described. The second embodiment of the present disclosure is different from the first embodiment of the present disclosure in the functions of the image correction unit 132. Accordingly, in the second embodiment of the present disclosure, functions of the image correction unit 132 will be mainly described. Note that, in the second embodiment of the present disclosure, functions of a server 10B will be described with reference to a functional configuration example of the server 10B shown in FIG. 4 as appropriate.

In the first embodiment of the present disclosure, there has been described an example of correcting the brightness of the image at the time of photographing using the temperature characteristics of the illumination light source. In the second embodiment of the present disclosure, there will be described an example of correcting brightness of an image at a time of photographing using a change rate of temperature characteristics of the illumination light source. That is, in the second embodiment of the present disclosure, the image correction unit 132 corrects the brightness of the image at the time of photographing on the basis of the temperature of the illumination light source at the time of photographing, the brightness of the image at the time of photographing, and the change rate of the temperature characteristics of the illumination light source.

Figure 10:
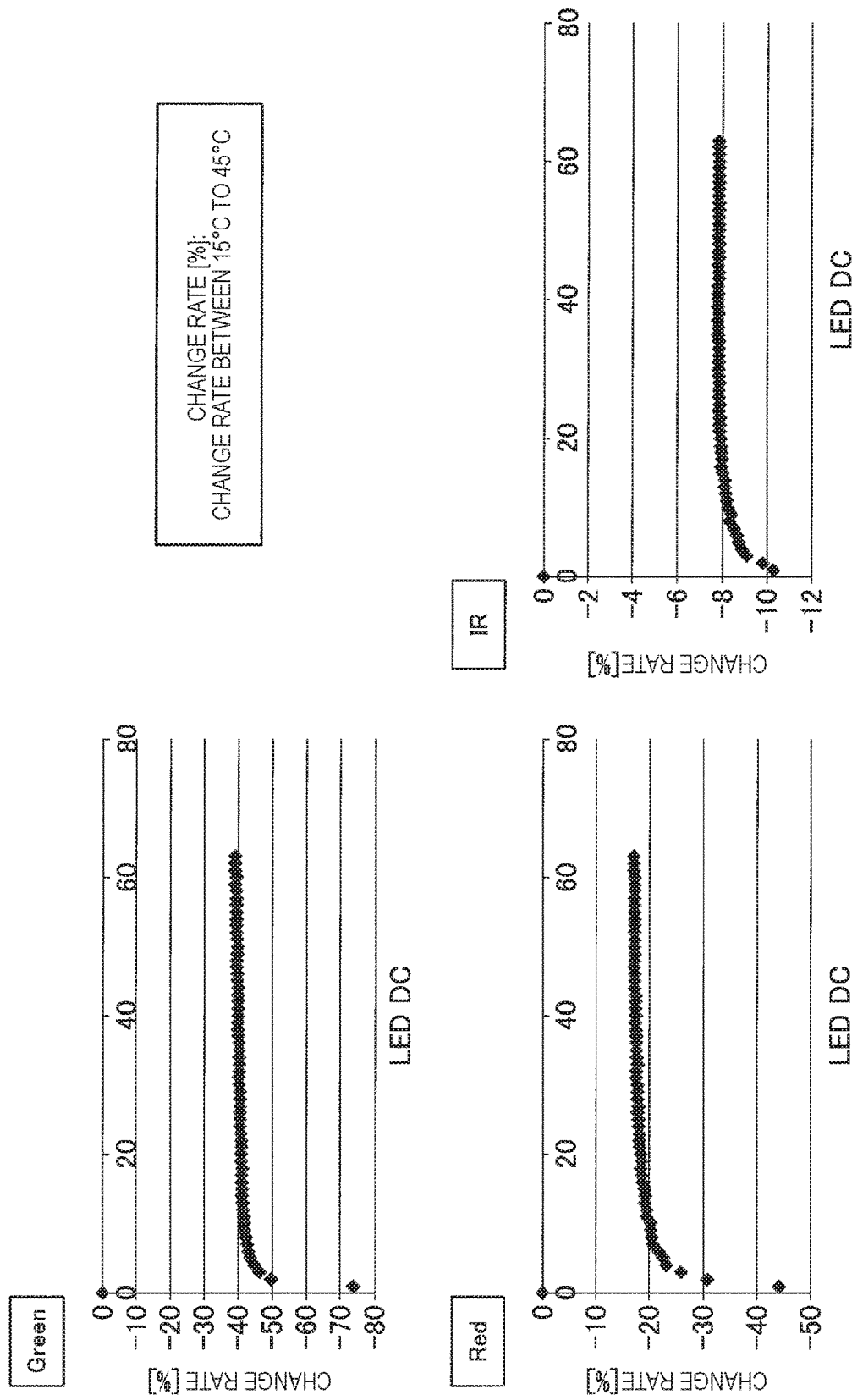
FIG. 10 is a diagram showing an example of a correspondence relationship between a DC value of each illumination light source (LED) and a change rate of a luminous intensity (or a radiant intensity).

FIG. 10 is a diagram showing an example of a correspondence relationship between a DC value of each illumination light source (LED) and a change rate of a luminous intensity (or a radiant intensity). In FIG. 10, for each of the green light source, the red light source, and the near-infrared light source, a change rate of the luminous intensity (or the radiant intensity) of the illumination light source (LED) corresponding to each DC value in the case where the temperature of the illumination light source is changed from 15° C. to 45° C. is shown. As shown in FIG. 10, the luminous intensity of the illumination light source (LED) changes in accordance with the DC value of the illumination light source (LED), but when the DC value increases to a certain extent, the change rate of the luminous intensity (or the radiant intensity) of the illumination light source (LED) may be linearly approximated as shown in the following formula (5).

[Math. 5]

$$\text{change\_rate}_i = \sum_{n=0}^{N} \text{change\_rate\_coef}_i^n \cdot (\text{led\_dc})^n \tag{5}$$

In formula (5), n represents a degree, and change_rate_coef represents a coefficient for each degree. Further, in the case where the change rate of the luminous intensity (or the radiant intensity) of the illumination light source (LED) is linearly approximated, the value of N is "1" in formula (5). The brightness of the image after correction from formula (5) may be calculated using the following formula (6). That is, the image correction unit 132 can correct the brightness of the image at the time of photographing on the basis of the following formula (4).

[Math. 6]

$$nI_i(x,y) = cIB_i(x,y) - cIB_i(x,y) \cdot (\text{change\_rate}_i/100) \cdot (\text{delta\_temp}_i/\text{limit\_delta\_temp}_i) \tag{6}$$

In formula (6), delta_temp and limit_delta_temp represent differences in temperature defined by the following formula (7) and formula (8), respectively.

[Math. 7]

$$\text{delta\_temp}_i = cT_i - pT_1 \tag{7}$$

[Math. 8]

$$\text{limit\_delta\_temp} = lT\max, -lT\min, \tag{8}$$

Heretofore, the second embodiment of the present disclosure has been described. Note that only the correction according to any one of the first embodiment of the present disclosure and the second embodiment of the present disclosure may be applied to all of the illumination light sources of the illumination unit 31, or the correction according to one embodiment may be applied to one or some of the illumination light source(s) of the illumination unit 31 and the correction according to the other embodiment may be applied to the rest of the illumination light source(s) of the illumination unit 31.

For example, to the illumination light source (for example, the illumination light source of green light) that requires a high DC level since the amount of LED light is small, the correction according to the second embodiment of the present disclosure may be applied. On the other hand, for example, to the illumination light source (for example, the illumination light source of red light) that does not require a high DC level since the amount of LED light is large, the correction according to the first embodiment of the present disclosure may be applied.

Further, a correction by which a similar effect can be obtained as the correction according to the first embodiment of the present disclosure described above may also be included in the correction according to the first embodiment of the present disclosure. Further, a correction by which a similar effect can be obtained as the correction according to the second embodiment of the present disclosure described above may also be included in the correction according to the second embodiment of the present disclosure.

3. DESCRIPTION OF THIRD EMBODIMENT

Figure 11:
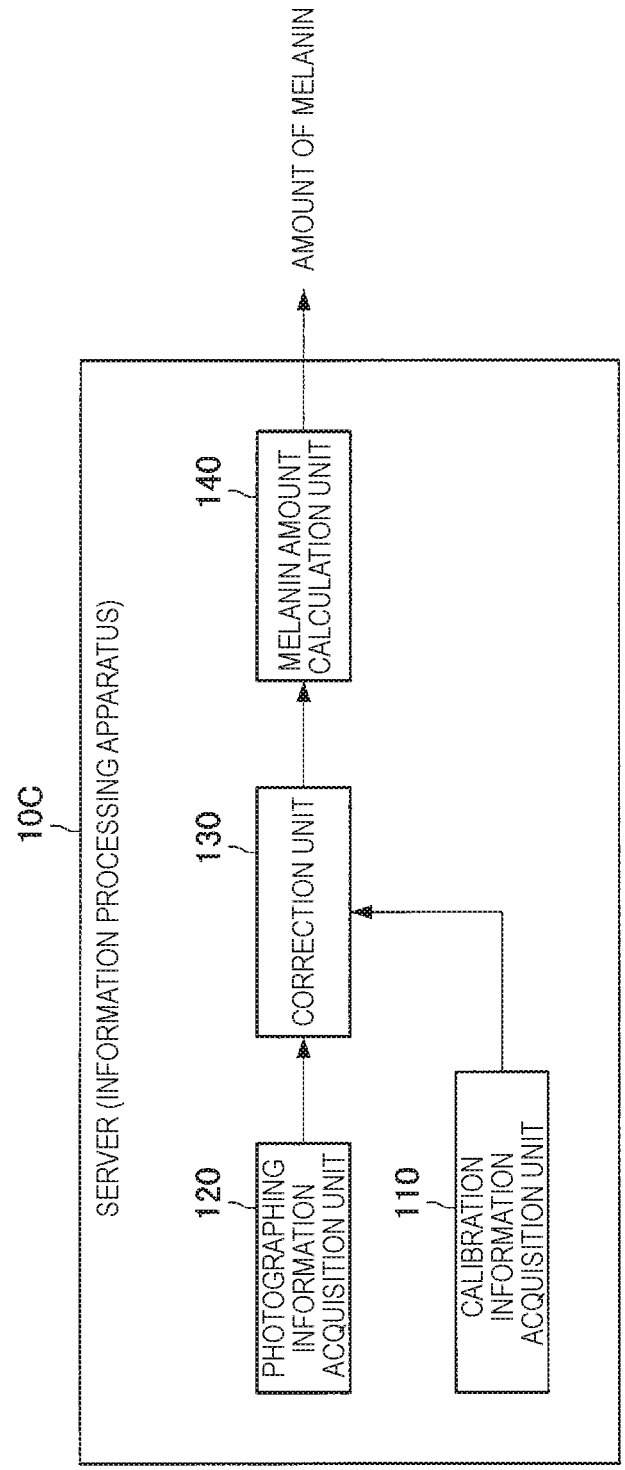
FIG. 11 is a diagram showing a functional configuration example of a server according to a third embodiment of the present disclosure.

Subsequently, a third embodiment of the present disclosure will be described. FIG. 11 is a diagram showing a functional configuration example of a server 10C according to the third embodiment of the present disclosure. As shown in FIG. 11, the third embodiment of the present disclosure is different from the first embodiment and the second embodiment of the present disclosure in that a melanin amount calculation unit 140 is included. Accordingly, in the third embodiment of the present disclosure, functions of the melanin amount calculation unit 140 will be mainly described.

Figure 12:
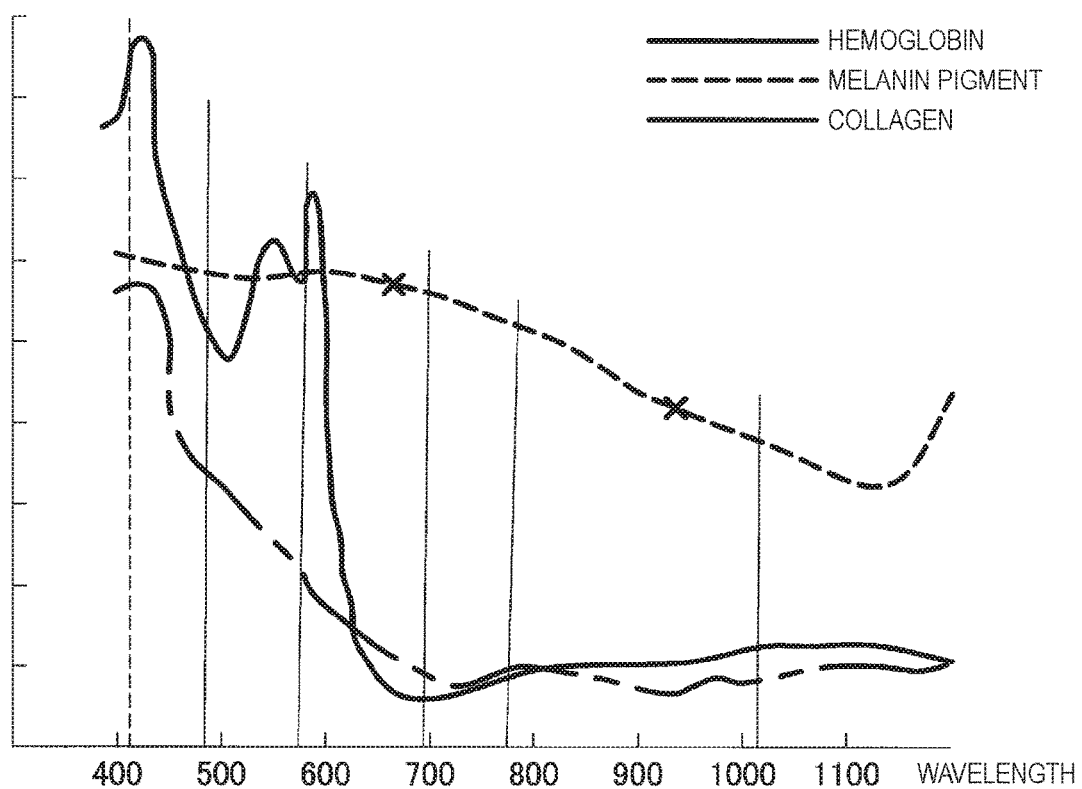
FIG. 12 is a diagram showing light absorption characteristics of a melanin pigment and other components (hemoglobin and collagen).

The melanin amount calculation unit 140 calculates an amount of melanin included in a subject (such as skin) on the basis of an image after brightness correction. Here, light absorption characteristics of melanin will be described. FIG. 12 is a diagram showing light absorption characteristics of a melanin pigment and other components (hemoglobin and collagen). As shown in FIG. 12, melanin is known to show light absorption characteristics that declines in value from the red light wavelength range to the near-infrared light wavelength range.

The melanin amount calculation unit 140 can calculate an amount of melanin MX using the light absorption characteristics of melanin, on the basis of an average value of an image after brightness correction under the red light source and an average value of an image after brightness correction under the near-infrared light source. A specific example of calculating the amount of melanin MX is as shown in the following formula (9).

[Math. 9]

$$MX = A_{MX'}(\log(\overline{nI_{IR}}) - \log(\overline{nI_R})) + B_{MX} \quad (9)$$

Figure 13:
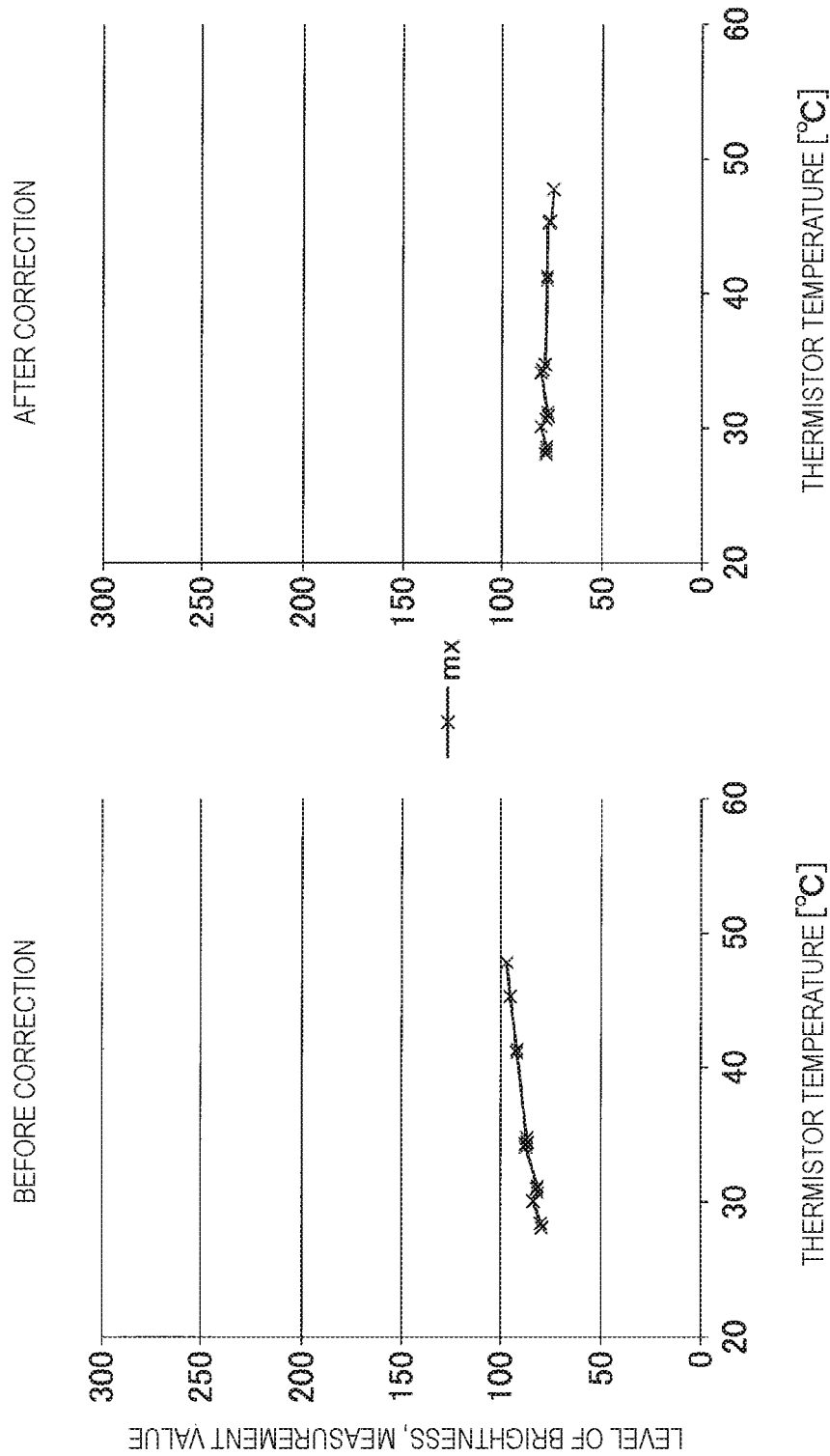
FIG. 13 is a diagram showing an example of a relationship between a temperature (thermistor temperature) of an illumination light source and an amount of melanin before and after brightness correction on an image.

In formula (9), $A_{MX}$ and $B_{MX}$ represent parameters, respectively, for calculating the amount of melanin, and an overline represents an average value. FIG. 13 is a diagram showing an example of a relationship between a temperature (thermistor temperature) of an illumination light source and an amount of melanin before and after brightness correction on an image. Formula (9) is used for calculating the amount of melanin. In the figure, "mx" represents the case where a subject to be measured is melanin.

In the example shown in FIG. 13, "before correction" shows an example of a relationship between the thermistor temperature at the time of photographing the same target object while changing the temperature of each illumination light source and the amount of melanin before correction. On the other hand, "after correction" shows an example of a relationship between the thermistor temperature at the time of photographing the same target object while changing the temperature and the amount of melanin after correction. As shown in FIG. 13, before brightness correction on the image, the amount of melanin increases with increase in temperature, however, after brightness correction on the image, the increase in the amount of melanin in accordance with the temperature can be suppressed (the amount of melanin can be calculated more accurately).

Note that, in the description above, an example in which the brightness of the image at the time of photographing is corrected by the correction unit 130 has been described. However, the brightness of the image at the time of photographing may be corrected by the melanin amount calculation unit 140. In such a case, the melanin amount calculation unit 140 performs the correction only on the image(s) that is(/are) used for calculating the amount of melanin (in the above example, the images photographed under the red light source and the near-infrared light source, respectively), and hence, the throughput necessary for the brightness correction can be reduced.

Heretofore, the third embodiment of the present disclosure has been described.

4. DESCRIPTION OF FOURTH EMBODIMENT

Figure 14:
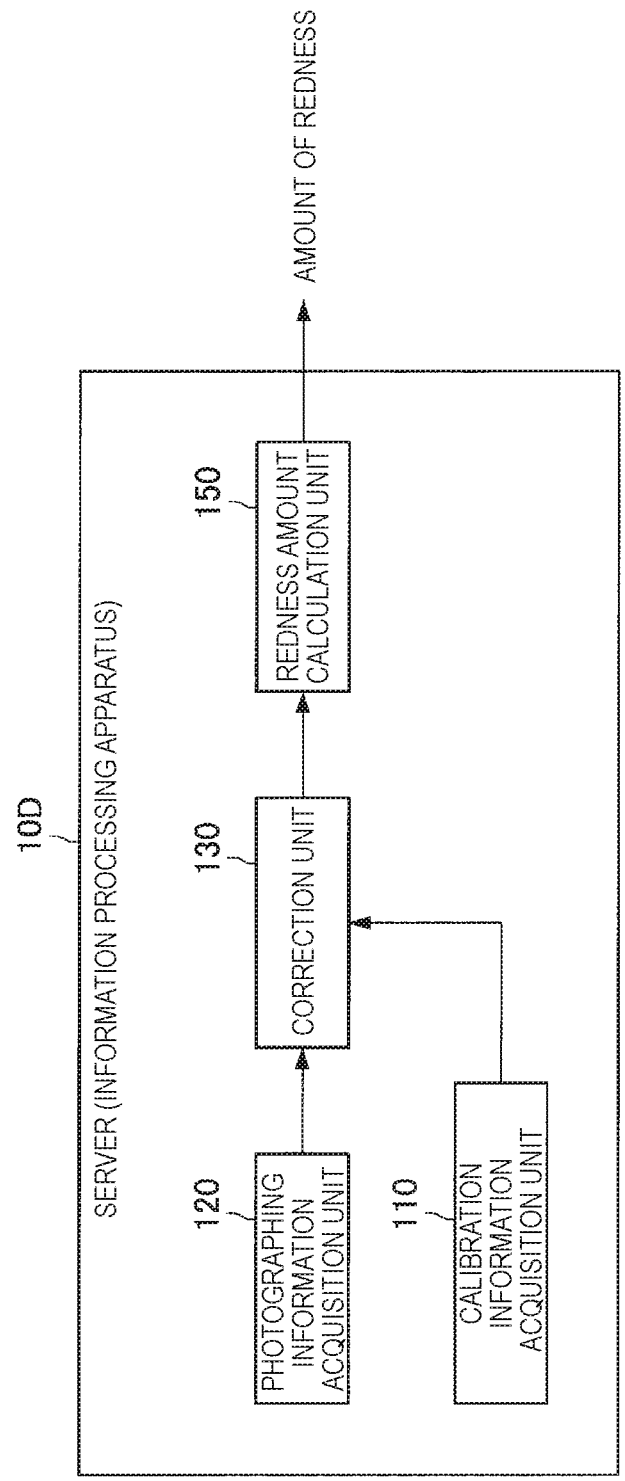
FIG. 14 is a diagram showing a functional configuration example of a server according to a fourth embodiment of the present disclosure.

Subsequently, a fourth embodiment of the present disclosure will be described. FIG. 14 is a diagram showing a functional configuration example of a server 10D according to the fourth embodiment of the present disclosure. As shown in FIG. 14, the fourth embodiment of the present disclosure is different from the first embodiment and the second embodiment of the present disclosure in that a redness amount calculation unit 150 is included. Accordingly, in the fourth embodiment of the present disclosure, functions of the redness amount calculation unit 150 will be mainly described.

Figure 15:
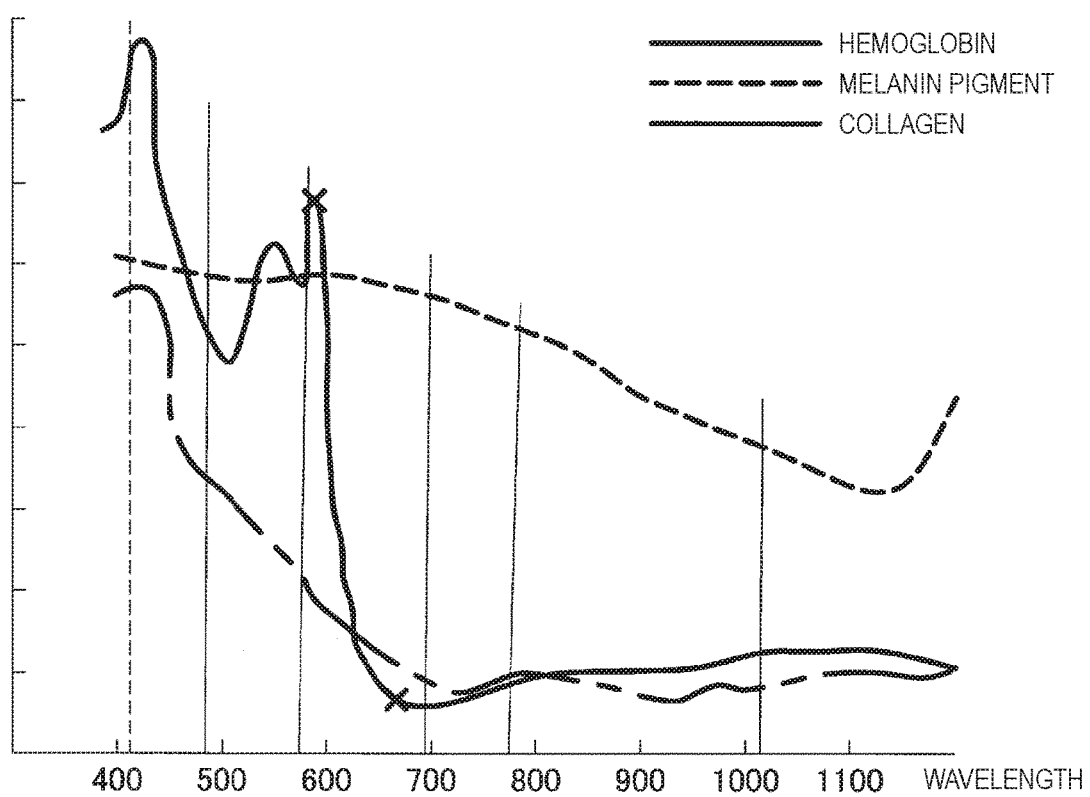
FIG. 15 is a diagram showing light absorption characteristics of hemoglobin and other components (a melanin pigment and collagen).

The redness amount calculation unit 150 calculates an amount of redness included in a subject (such as skin) on the basis of an image after brightness correction. Here, the redness of the skin generally originates from a hemoglobin component included in the skin. Here, light absorption characteristics of hemoglobin will be described. FIG. 15 is a diagram showing light absorption characteristics of hemoglobin and other components (a melanin pigment and collagen). As shown in FIG. 15, hemoglobin is known to show light absorption characteristics that declines in value from the green light wavelength range to the red light wavelength range.

The melanin amount calculation unit 140 can calculate an amount of redness EX using the light absorption characteristics of hemoglobin, on the basis of an average value of an image after brightness correction under the green light source and an average value of an image after brightness correction under the red light source. A specific example of calculating the amount of redness EX is as shown in the following formula (10).

[Math. 10]

$$EX = A_{EX'}(\log(\overline{nI_R}) - \log(\overline{nI_G})) + B_{EX} \quad (10)$$

Figure 16:
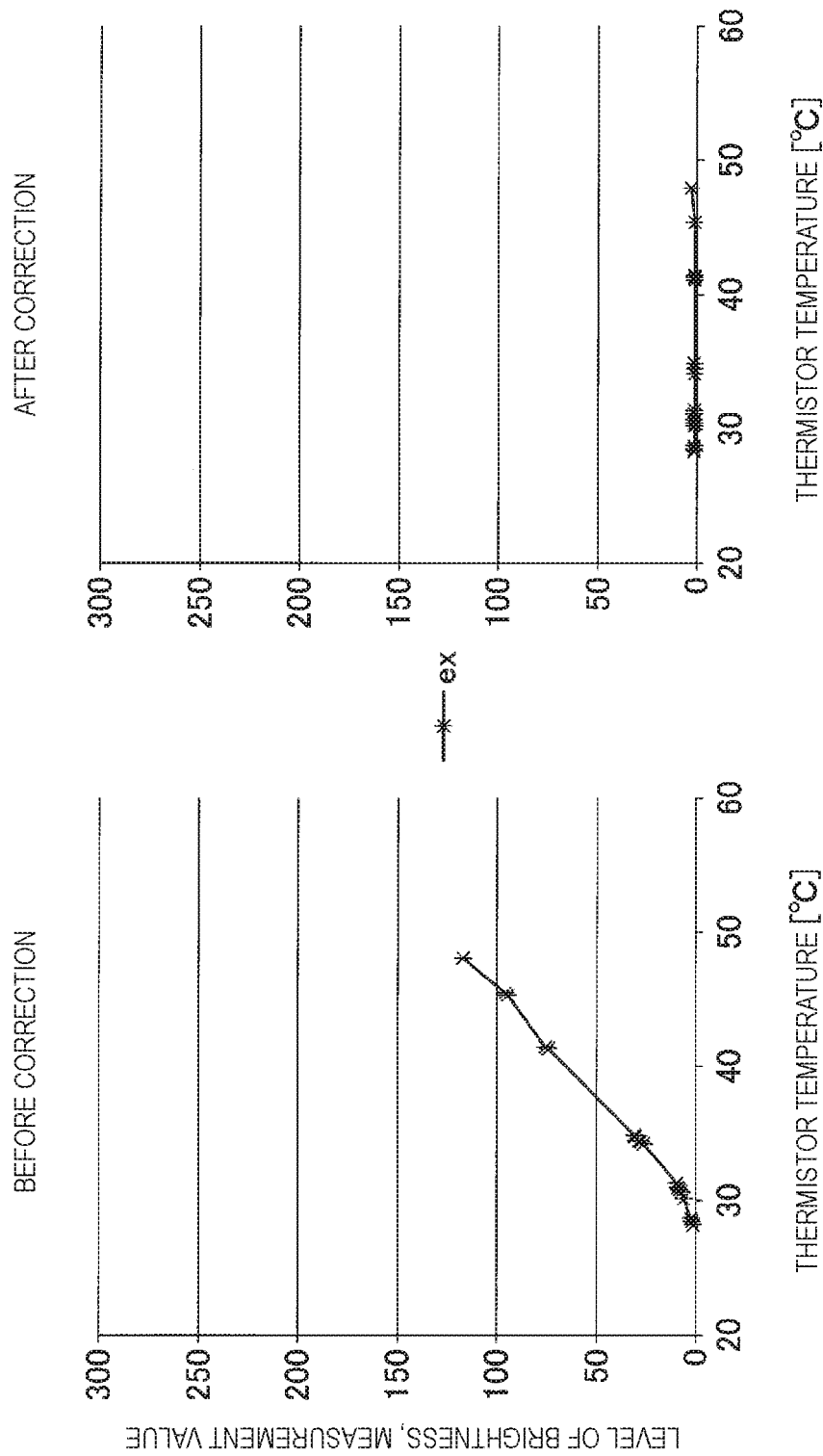
FIG. 16 is a diagram showing an example of a relationship between a temperature (thermistor temperature) of an illumination light source and an amount of redness before and after brightness correction on an image.

In formula (10), $A_{EX}$ and $B_{EX}$ represent parameters, respectively, for calculating the amount of redness, and an overline represents an average value. FIG. 16 is a diagram showing an example of a relationship between a temperature (thermistor temperature) of an illumination light source and an amount of redness before and after brightness correction on an image. Formula (10) is used for calculating the amount of redness. In the figure, "ex" represents the case where a subject to be measured is redness.

In the example shown in FIG. 16, "before correction" shows an example of a relationship between the thermistor temperature at the time of photographing the same target object while changing the temperature of each illumination light source and the amount of redness before correction. On the other hand, "after correction" shows an example of a relationship between the thermistor temperature at the time of photographing the same target object while changing the temperature and the amount of redness after correction. As shown in FIG. 16, before brightness correction on the image, the amount of redness increases with increase in temperature, however, after brightness correction on the image, the increase in the amount of redness in accordance with the temperature can be suppressed (the amount of redness can be calculated more accurately).

Note that, in the description above, an example in which the brightness of the image at the time of photographing is corrected by the correction unit 130 has been described. However, the brightness of the image at the time of photographing may be corrected by the redness amount calculation unit 150. In such a case, the redness amount calculation unit 150 performs the correction only on the image(s) that is(/are) used for calculating the amount of redness (in the above example, the images photographed under the green light source and the red light source, respectively), and hence, the throughput necessary for the brightness correction can be reduced.

Heretofore, the fourth embodiment of the present disclosure has been described. Note that, in the third embodiment of the present disclosure, an example has been described in which the amount of melanin included in the subject is calculated on the basis of the image after brightness correction, and in the fourth embodiment of the present disclosure, an example has been described in which the amount of redness included in the subject is calculated on the basis of the image after brightness correction. However, an amount of another component included in the subject may be calculated on the basis of the image after brightness correction. For example, the brightness the skin itself may be calculated on the basis of the image after brightness correction with respect to the image photographed under the white light source. Also in such a case, after brightness correction on the image, the change in the amount of the skin in accordance with the temperature can be suppressed (the brightness of the skin can be calculated more accurately).

5. DESCRIPTION OF FIFTH EMBODIMENT

Subsequently, a fifth embodiment of the present disclosure will be described. In the first embodiment of the present disclosure and the second embodiment of the present disclosure, examples in which the same brightness correction is performed on the entire image have been described. However, the same brightness correction is not necessarily performed over the entire image. In the fifth embodiment of the present disclosure, an example in which correction is performed in a manner that a contrast of a distribution of melanin is emphasized will be described.

Figure 17:
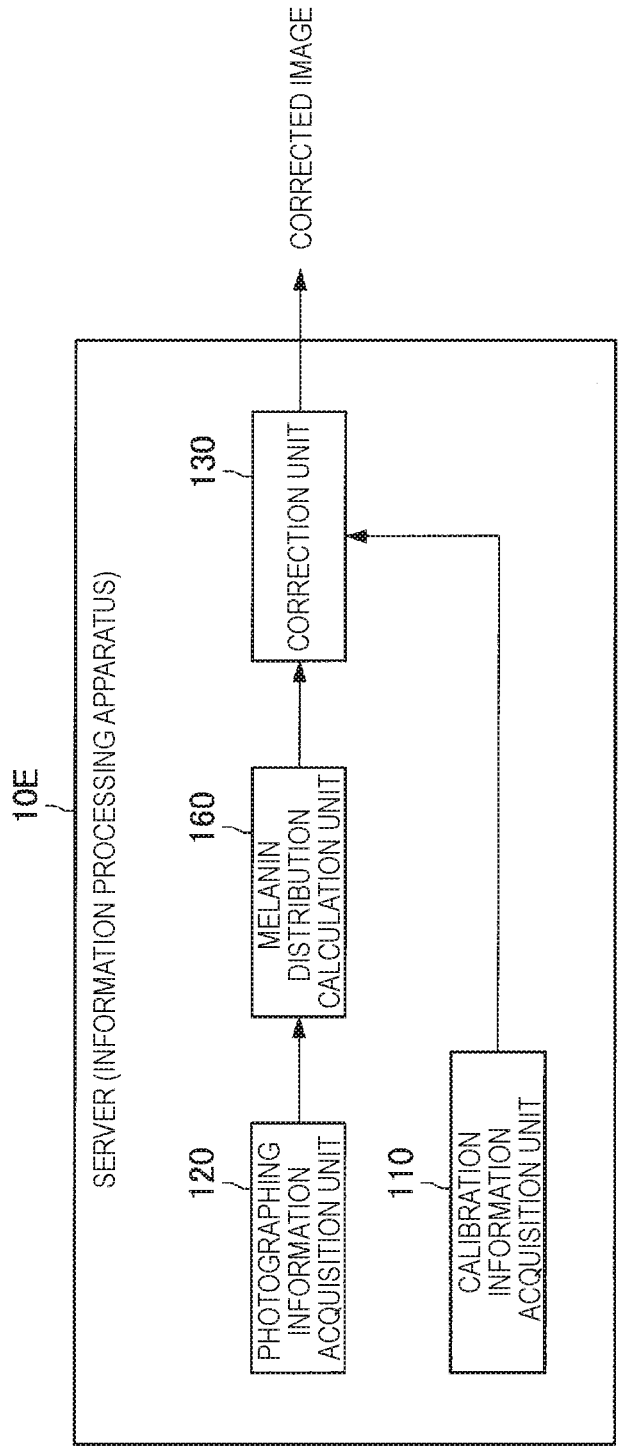
FIG. 17 is a diagram showing a functional configuration example of a server according to a fifth embodiment of the present disclosure.

FIG. 17 is a diagram showing a functional configuration example of a server 10E according to the fifth embodiment of the present disclosure. As shown in FIG. 17, the fifth embodiment of the present disclosure is different from the first embodiment and the second embodiment of the present disclosure in that a melanin distribution calculation unit 160 is included and the functions of the correction unit 130 is changed. Accordingly, in the fifth embodiment of the present disclosure, functions of the melanin distribution calculation unit 160 and functions of the correction unit 130 will be mainly described.

The melanin distribution calculation unit 160 calculates a distribution of melanin included in a subject on the basis of an image at a time of photographing. For example, the melanin distribution calculation unit 160 can calculate the distribution of melanin included in the subject by applying the above formula (9) to each pixel of the image at the time of photographing (to be more specific, by replacing "an average value of an image after brightness correction under the red light source" and "an average value of an image after brightness correction under the near-infrared light source" of the above formula (9) with "each pixel at the time of photographing under the red light source" and "each pixel at the time of photographing under the near-infrared light source", respectively).

Subsequently, the image correction unit 132 corrects the image at the time of photographing in a manner that the contrast of the distribution of melanin in the image at the time of photographing is emphasized. For example, the image correction unit 132 can correct the image at the time of photographing in a manner that the contrast of the distribution of melanin in the image at the time of photographing in accordance with the following formula (11) and formula (12).

[Math. 11]

$$nI_R(x,y)=cI_R(x,y)-\alpha_R^{MX}(x,y)\cdot\text{temp\_intensity\_slope}_R\cdot\text{delta\_temp}_R\cdot pB_R/(\text{intensity}_R\cdot\text{led\_num}_R) \quad (11)$$

[Math. 12]

$$nI_{IR}(x,y)=cI_{IR}(x,y)-\alpha_{IR}^{MX}(x,y)\cdot\text{temp\_intensity\_slope}_{IR}\cdot\text{delta\_temp}_{IR}\cdot pB_{IR}/(\text{intensity}_{IR}\cdot\text{led\_num}_{IR}) \quad (12)$$

Figure 18:
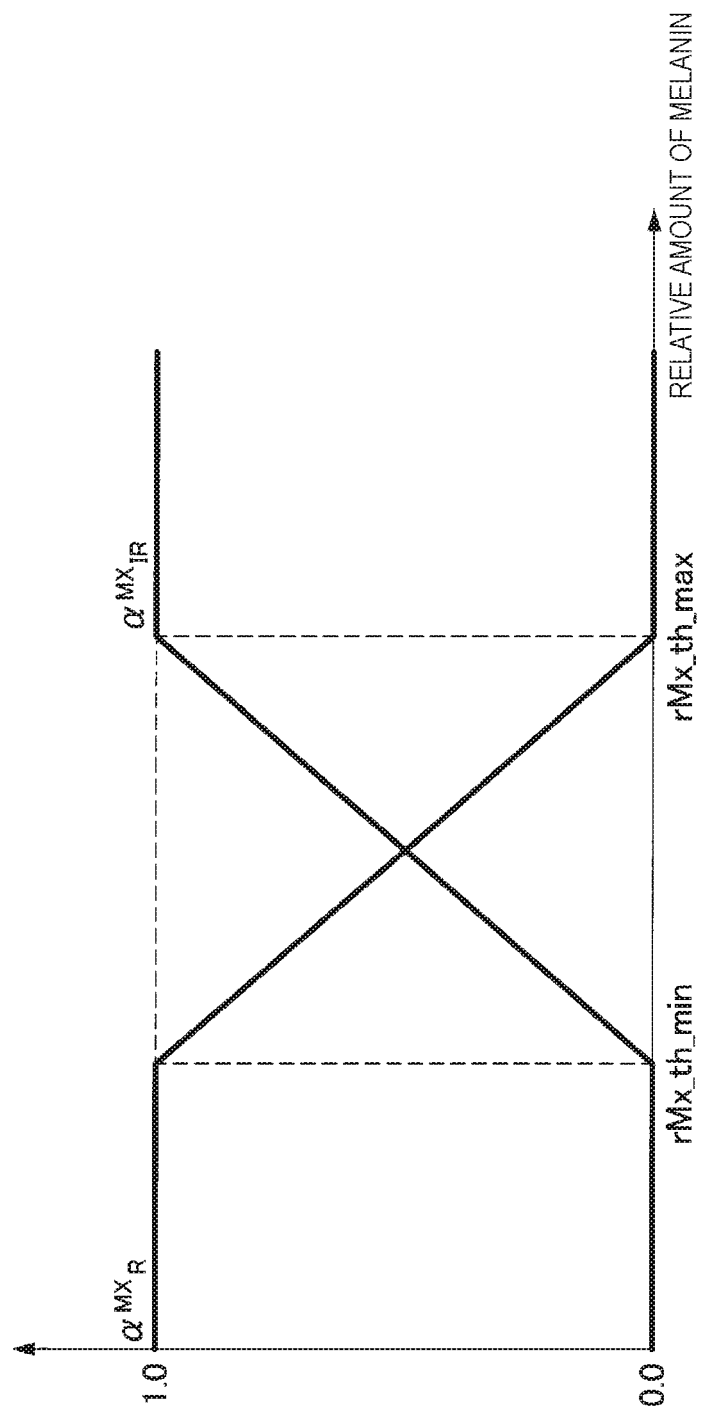
FIG. 18 is a diagram showing an example of a relationship between a relative amount of melanin and a coefficient.

In the above formulae, $\alpha^{MX}$ represents a coefficient that changes with a relative amount of melanin. FIG. 18 is a diagram showing an example of a relationship between the relative amount of melanin and the coefficient $\alpha^{MX}$. The subscript R and the subscript IR attached to coefficients represent the cases where the red light source and the near-infrared light source are used as the illumination light sources, respectively.

Subsequently, with reference to FIG. 19, the effects achieved by the fifth embodiment of the present disclosure will be described. FIG. 19 is a diagram showing an example of images before and after brightness correction according to the fifth embodiment of the present disclosure. "Before correction" represents an example of an image before brightness correction, and "after correction" represents an example of an image after brightness correction. As shown in FIG. 19, with the correction in such a manner that the contrast of the distribution of melanin is emphasized, the display can be performed in a way that a user can easily recognize the presence of melanin.

Note that, in the description above, an example in which the brightness of the image at the time of photographing is corrected by the correction unit 130 has been described. However, the brightness of the image at the time of photographing may be corrected by the melanin distribution calculation unit 160. In such a case, the melanin distribution calculation unit 160 performs the correction only on the image(s) that is(/are) used for calculating the amount of melanin (in the above example, the images photographed under the red light source and the near-infrared light source, respectively), and hence, the throughput necessary for the brightness correction can be reduced.

6. DESCRIPTION OF SIXTH EMBODIMENT

Subsequently, a sixth embodiment of the present disclosure will be described. In the first embodiment of the present disclosure and the second embodiment of the present disclosure, examples in which the same brightness correction is performed on the entire image have been described. However, the same brightness correction is not necessarily performed over the entire image. In the sixth embodiment of the present disclosure, an example in which correction is performed in a manner that a contrast of a distribution of redness is emphasized will be described.

Figure 20:
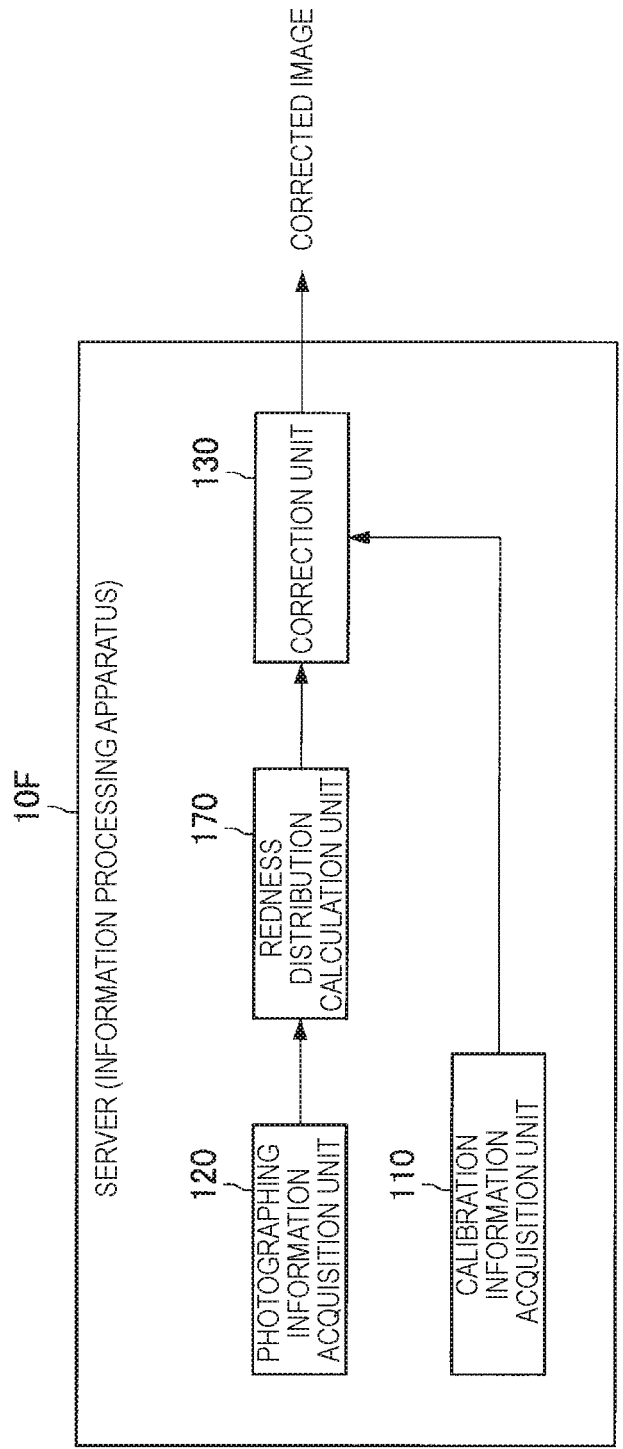
FIG. 20 is a diagram showing a functional configuration example of a server according to a sixth embodiment of the present disclosure.

FIG. 20 is a diagram showing a functional configuration example of a server 10F according to the sixth embodiment of the present disclosure. As shown in FIG. 20, the sixth embodiment of the present disclosure is different from the first embodiment and the second embodiment of the present disclosure in that a redness distribution calculation unit 170 is included and the functions of the correction unit 130 is changed. Accordingly, in the sixth embodiment of the present disclosure, functions of the redness distribution calculation unit 170 and functions of the correction unit 130 will be mainly described.

The redness distribution calculation unit 170 calculates a distribution of redness included in a subject on the basis of an image at a time of photographing. For example, the redness distribution calculation unit 170 can calculate the distribution of redness included in the subject by applying the above formula (9) to each pixel of the image at the time of photographing (to be more specific, by replacing "an average value of an image after brightness correction under the red light source" and "an average value of an image after brightness correction under the green light source" of the above formula (10) with "each pixel at the time of photographing under the red light source" and "each pixel at the time of photographing under the green light source", respectively).

Subsequently, the image correction unit 132 corrects the image at the time of photographing in a manner that the contrast of the distribution of redness in the image at the time of photographing is emphasized. For example, the image correction unit 132 can correct the image at the time of photographing in a manner that the contrast of the distribution of redness in the image at the time of photographing in accordance with the following formula (13) and formula (14).

[Math. 13]

$$nI_G(x,y)=cI_G(x,y)-\alpha_G^{EX}(x,y)\cdot\text{temp\_intensity\_slope}_G\cdot\text{delta\_temp}_G\cdot pB_G/(\text{intensity}_G\cdot\text{led\_num}_G) \quad (13)$$

[Math. 14]

$$nI_R(x,y)=cI_R(x,y)-\alpha_R^{EX}(x,y)\cdot\text{temp\_intensity\_slope}_R\cdot\text{delta\_temp}_R\cdot pB_R/(\text{intensity}_R\cdot\text{led\_num}_R) \quad (14)$$

Figure 21:
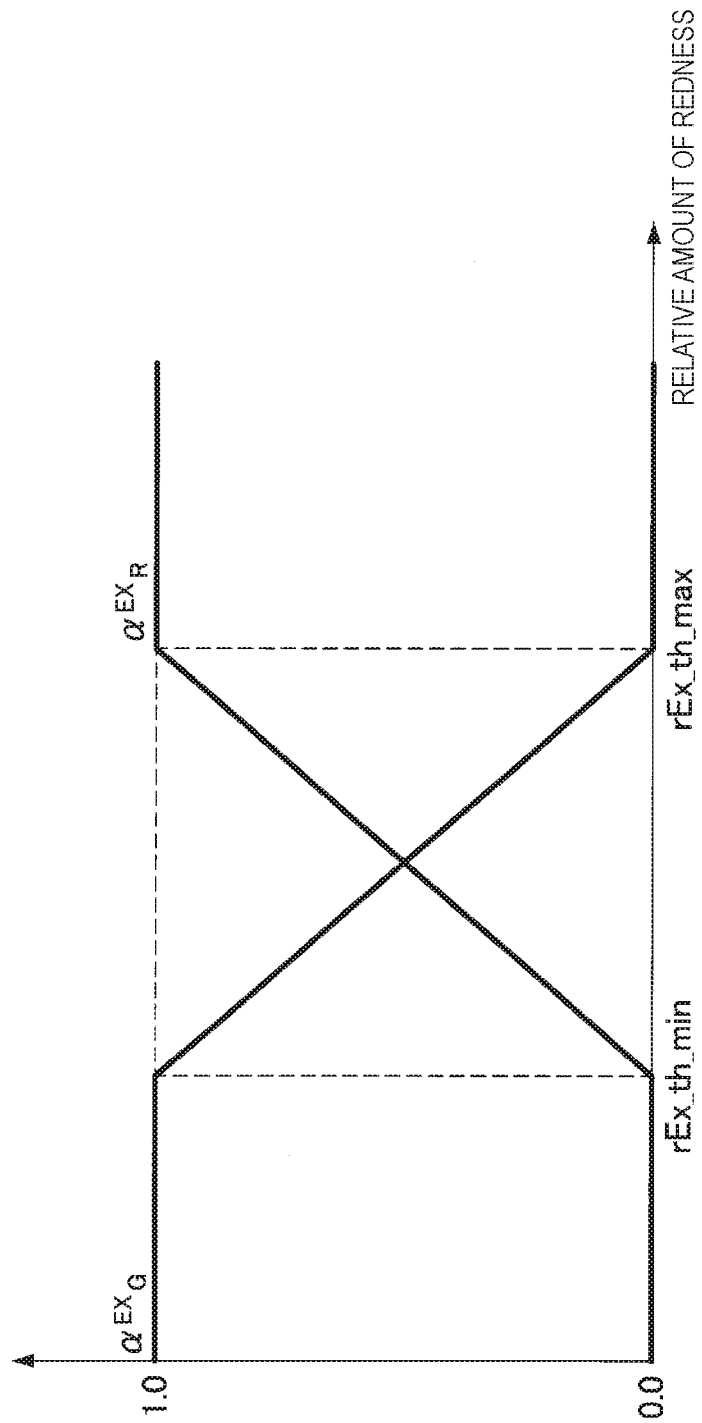
FIG. 21 is a diagram showing an example of a relationship between a relative amount of redness and a coefficient.

In the above formulae, $\alpha^{EX}$ represents a coefficient that changes with a relative amount of redness. FIG. 21 is a diagram showing an example of a relationship between the relative amount of redness and the coefficient $\alpha^{EX}$. The subscript G and the subscript R attached to coefficients represent the cases where the green light source and the red light source are used as the illumination light sources, respectively.

Subsequently, with reference to FIG. 22, the effects achieved by the sixth embodiment of the present disclosure will be described. FIG. 22 is a diagram showing an example of images before and after brightness correction according to the sixth embodiment of the present disclosure. "Before correction" represents an example of an image before brightness correction, and "after correction" represents an example of an image after brightness correction. As shown in FIG. 22, with the correction in such a manner that the contrast of the distribution of redness is emphasized, the display can be performed in a way that a user can easily recognize the presence of redness.

Note that, in the description above, an example in which the brightness of the image at the time of photographing is corrected by the correction unit 130 has been described. However, the brightness of the image at the time of photographing may be corrected by the redness distribution calculation unit 170. In such a case, the redness distribution calculation unit 170 performs the correction only on the image(s) that is(/are) used for calculating the amount of redness (in the above example, the images photographed under the green light source and the red light source, respectively), and hence, the throughput necessary for the brightness correction can be reduced.

7. HARDWARE CONFIGURATION EXAMPLE OF INFORMATION PROCESSING APPARATUS

Figure 23:
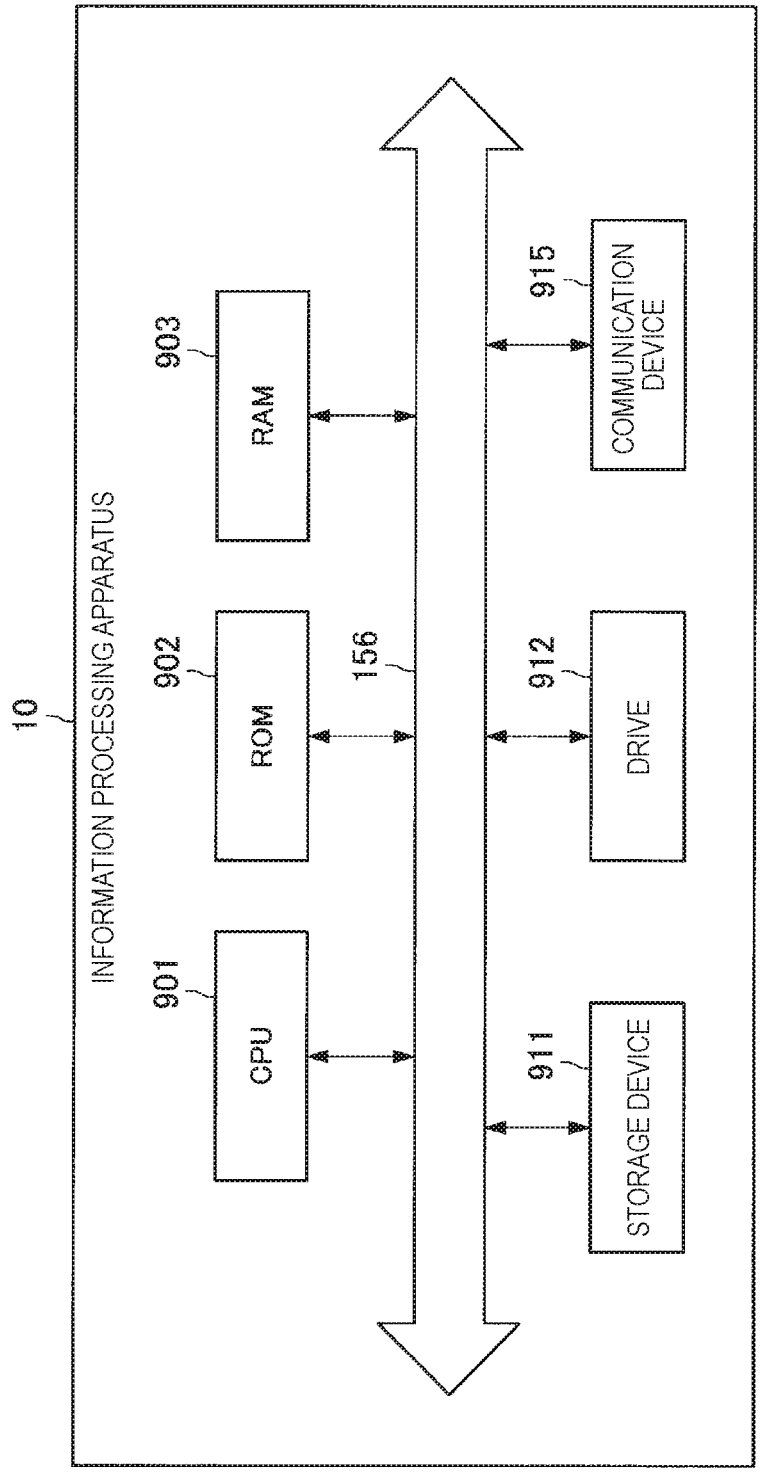
FIG. 23 is a diagram showing a hardware configuration example of an information processing apparatus according to an embodiment of the present disclosure.

Subsequently, a hardware configuration example of the information processing apparatus 10 according to an embodiment of the present disclosure will be described. FIG. 23 is a diagram showing the hardware configuration example of the information processing apparatus 10 according to an embodiment of the present disclosure. However, the hardware configuration example shown in FIG. 23 merely shows an example of the hardware configuration of the information processing apparatus 10. Accordingly, the hardware configuration of the information processing apparatus 10 is not limited to the example shown in FIG. 23.

As shown in FIG. 23, the information processing apparatus 10 includes a central processing unit (CPU) 901, read only memory (ROM) 902, random access memory (RAM) 903, a storage device 911, a drive 912, and a communication device 915.

The CPU 901 functions as an arithmetic processing device and a control device, and controls entire operation of the information processing apparatus 10 in accordance with various programs. Further, the CPU 901 may be a microprocessor. The ROM 902 stores a program, a calculation parameter, and the like used by the CPU 901. The RAM 903 temporarily stores a program used in execution of the CPU 901, a parameter varying as appropriate during the execution, and the like. They are connected with each other via the host bus 156 configured from a CPU bus or the like.

The storage device 911 is an example of a storage unit of the information processing apparatus 10, and is a device for storing data. The storage device 911 may include, for example, a storage medium, a recording device for recording data in the storage medium, a reading device for reading out the data from the storage medium, and a deletion device for deleting the data recorded in the storage medium. The storage device 911 stores a program executed by the CPU 901 and various data.

The drive 912 is a reader/writer for the storage medium and is built in or externally attached to the information processing apparatus 10. The drive 912 reads out information recorded in a removable storage medium which is mounted thereto, such as a magnetic disk, an optical disc, a magneto-optical disk, or semiconductor memory, and outputs the information to the RAM 903. Further, the drive 912 can also write the information in the removable storage medium.

The communication device 915 communicates via a network (or directly) with an external device. The communication device 915 may be an interface for radio communication, and may include a communication antenna, a radio frequency (RF) circuit, and a base band processor, for example. Specific examples of the interface for radio communication include communication units such as modems that support communication schemes such as code division multiple access (CDMA), wideband code division multiple access (W-CDMA), long term evolution (LTE), and wireless fidelity (Wi-fi) (registered trademark).

Further, the communication device 915 may be an interface for wired communication, and may include a connection terminal, a transmission line, and other circuits for communication processing, for example. The CPU 901 and the communication device 915 may be configured on one chip, or may be provided as separate devices. Although not shown in FIG. 23, the information processing apparatus 10 may be driven by power supplied from a power source such as a rechargeable battery, for example, and the power source may be attachable to and detachable from the information processing apparatus 10.

Heretofore, the hardware configuration example of the information processing apparatus 10 according to an embodiment of the present disclosure has been described.

8. CONCLUSION

As described above, according to an embodiment of the present disclosure, there is provided the information processing apparatus 10 including the photographing information acquisition unit 120 configured to acquire an image at the time of photographing photographed by the camera 30 and a temperature of an illumination light source at the time of photographing, and the correction unit 130 configured to correct a brightness of the image at the time of photographing or an exposure time period of the camera 30 on the basis of the temperature of the illumination light source at the time of photographing, the brightness of the image at the time of photographing, and temperature characteristics of the illumination light source, the temperature characteristics having been prepared in advance. According to such a configuration, the brightness of the photographed image can be adjusted with a technique that does not include driving and controlling the illumination light source.

Hereinafter, a difference between the technology written in Patent Literature and the technology according to an embodiment of the present disclosure will be described in detail. First, as the first technology, there is disclosed a technology including measuring temperature of an illumination light source, and checking the measured temperature against temperature characteristics of the illumination light source, thereby driving the light source such that the luminous intensity of the illumination light source becomes optimum (for example, see Patent Literature 1). However, in the technology written in Patent Literature 1, since it is necessary to drive and control the illumination light source, it takes time to stabilize an electric current.

As a second technology, there is given auto exposure (AE). However, in the case where the AE is used, multiple subjects having different brightnesses from each other have the same brightness in a photographed image. Accordingly, in the case where the AE is used, it is difficult to obtain a photographed image in which accurate brightnesses of the subjects are reflected. On the other hand, according to an embodiment of the present disclosure, a photographed image in which accurate brightnesses of the subjects are reflected can be obtained.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the above description, the example in which the correction unit 130 corrects the brightness of the image at the time of photographing has been described. According to such a correction, the brightness of the image at the time of photographing may be corrected. However, the correction unit 130 may also correct an exposure time period of the camera 30 instead of the brightness of the image at the time of photographing. If the exposure time period of the camera 30 is corrected, although the brightness of the image itself at the time of photographing is not corrected, the brightness in the image photographed by the camera 30 in which the exposure time period has been corrected is corrected.

Further, it is also possible to create a program for causing hardware such as a CPU, ROM, and RAM, which are built in a computer, to exhibit substantially the same functions as the respective functions of the information processing apparatus 10 described above. Further, there is also provided a computer-readable recording medium having the program recorded thereon.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a photographing information acquisition unit configured to acquire an image at a time of photographing photographed by a camera and a temperature of an illumination light source at the time of photographing; and a correction unit configured to correct a brightness of the image at the time of photographing or an exposure time period of the camera on the basis of the temperature of the illumination light source at the time of photographing, the brightness of the image at the time of photographing, and temperature characteristics of the illumination light source, the temperature characteristics having been prepared in advance.

(2)

The information processing apparatus according to (1), wherein the correction unit corrects the brightness of the image at the time of photographing.

(3)

The information processing apparatus according to (2), wherein the correction unit corrects the brightness of the image at the time of photographing on the basis of the temperature of the illumination light source at the time of photographing, a temperature of the illumination light source at a time of calibration, the brightness of the image at the time of photographing, a brightness of the image at the time of calibration, and the temperature characteristics of the illumination light source.

(4)

The information processing apparatus according to (3), further including:

a calibration information acquisition unit configured to acquire the temperature of the illumination light source at the time of calibration and the brightness of the image at the time of calibration photographed by the camera.

(5)

The information processing apparatus according to (3) or (4), wherein the brightness of the image at the time of calibration is a brightness of an image at a time of calibration in which a reference material is photographed by the camera.

(6)

The information processing apparatus according to any one of (3) to (5), wherein the correction unit corrects the brightness of the image at the time of photographing on the basis of a difference between the temperature of the illumination light source at the time of photographing and the temperature of the illumination light source at the time of calibration, the brightness of the image at the time of photographing, the brightness of the image at the time of calibration, and the temperature characteristics of the illumination light source.

(7)

The information processing apparatus according to any one of (3) to (6), wherein the temperature characteristics of the illumination light source indicates a luminous intensity or a radiant intensity of the illumination light source corresponding to the temperature of the illumination light source.

(8)

The information processing apparatus according to (7), wherein the temperature characteristics of the illumination light source depends on a driving current of the illumination light source, and the correction unit corrects the brightness of the image at the time of photographing on the basis of the temperature of the illumination light source at the time of photographing, the temperature of the illumination light source at the time of calibration, the brightness of the image at the time of photographing, the brightness of the image at the time of calibration, the driving current of the illumination light source, and the temperature characteristics of the illumination light source.

(9)

The information processing apparatus according to any one of (3) to (6), wherein the correction unit corrects the brightness of the image at the time of photographing on the basis of the temperature of the illumination light source at the time of photographing, the brightness of the image at the time of photographing, and a change rate of the temperature characteristics of the illumination light source.

(10)

The information processing apparatus according to any one of (1) to (9), further including:

a melanin amount calculation unit configured to calculate an amount of melanin included in a subject on the basis of an image after brightness correction.

(11)

The information processing apparatus according to (10), wherein the melanin amount calculation unit calculates the amount of melanin on the basis of an average value of an image after brightness correction under a red light source and an average value of an image after brightness correction under a near-infrared light source.

(12)

The information processing apparatus according to any one of (1) to (11), further including:

a redness amount calculation unit configured to calculate an amount of redness included in a subject on the basis of an image after brightness correction.

(13)

The information processing apparatus according to (12), wherein the redness amount calculation unit calculates the amount of redness on the basis of an average value of an image after brightness correction under a red light source and an average value of an image after brightness correction under a green light source.

(14)

The information processing apparatus according to any one of (1) to (9), wherein the correction unit corrects the image at the time of photographing in a manner that a contrast of a distribution of melanin in the image at the time of photographing is emphasized.

(15)

The information processing apparatus according to (14), further including:

a melanin distribution calculation unit configured to calculate the distribution of melanin in the image at the time of photographing.

(16)

The information processing apparatus according to any one of (1) to (9), wherein the correction unit corrects the image at the time of photographing in a manner that a contrast of a distribution of an amount of redness in the image at the time of photographing is emphasized.

(17)

The information processing apparatus according to (16), further including:

a redness amount distribution calculation unit configured to calculate the distribution of the amount of redness in the image at the time of photographing.

(18)

The information processing apparatus according to (1), wherein the correction unit corrects the exposure time period of the camera.

(19)

An information processing method including:

acquiring an image at a time of photographing photographed by a camera and a temperature of an illumination light source at the time of photographing; and correcting, by a processor, a brightness of the image at the time of photographing or an exposure time period of the camera on the basis of the temperature of the illumination light source at the time of photographing, the brightness of the image at the time of photographing, and temperature characteristics of the illumination light source, the temperature characteristics having been prepared in advance.

(20)

A program for causing a computer to function as an information processing apparatus including:

a photographing information acquisition unit configured to acquire an image at a time of photographing photographed by a camera and a temperature of an illumination light source at the time of photographing; and a correction unit configured to correct a brightness of the image at the time of photographing or an exposure time period of the camera on the basis of the temperature of the illumination light source at the time of photographing, the brightness of the image at the time of photographing, and temperature characteristics of the illumination light source, the temperature characteristics having been prepared in advance.

REFERENCE SIGNS LIST 1 skin analysis system
10 (10A to 10F) server (information processing apparatus)
20 information processing terminal
30 camera
31 illumination unit
32 tube
33 housing
34 lens
35 image sensor
40 relay device
110 calibration information acquisition unit
111 image acquisition unit
112 brightness calculation unit
113 temperature acquisition unit
120 photographing information acquisition unit
121 image acquisition unit
122 temperature acquisition unit
130 correction unit
131 brightness calculation unit
132 image correction unit
140 melanin amount calculation unit
150 redness amount calculation unit
160 melanin distribution calculation unit
170 redness distribution calculation unit

The invention claimed is:

1. An information processing apparatus comprising:
a central processing unit (CPU) configured to:
acquire a first image photographed by an image capturing apparatus at a time of photographing operation;
acquire a first temperature of an illumination light source at the time of photographing operation; and
correct, one of a brightness of the first image at the time of photographing operation or an exposure time period of the image capturing apparatus, based on the first temperature of the illumination light source at the time of photographing operation, the brightness of the first image at the time of photographing operation, a second temperature of the illumination light source at a time of calibration, a brightness of a reference image at the time of calibration, and temperature characteristics of the illumination light source,
wherein the reference image is an image of a reference material photographed by the image capturing apparatus at the time of calibration, and
wherein the temperature characteristics of the illuminating light source are pre-set.

2. The information processing apparatus according to claim 1, wherein the CPU is further configured to:
acquire the second temperature of the illumination light source at the time of calibration; and
acquire the brightness of the reference image photographed by the image capturing apparatus at the time of calibration.

3. The information processing apparatus according to claim 1, wherein the CPU is further configured to correct the brightness of the first image at the time of photographing operation based on a difference between the first temperature of the illumination light source at the time of photographing operation and the second temperature of the illumination light source at the time of calibration, the brightness of the first image at the time of photographing operation, the brightness of the reference image at the time of calibration, and the temperature characteristics of the illumination light source.

4. The information processing apparatus according to claim 1, wherein the temperature characteristics of the illumination light source indicates one of a luminous intensity or a radiant intensity of the illumination light source corresponding to temperature of the illumination light source.

5. The information processing apparatus according to claim 4,
wherein the temperature characteristics of the illumination light source is based on a driving current of the illumination light source, and
wherein the CPU is further configured to correct the brightness of the image at the time of photographing operation based on the first temperature of the illumination light source at the time of photographing operation, the second temperature of the illumination light source at the time of calibration, the brightness of the first image at the time of photographing operation, the brightness of the reference image at the time of calibration, the driving current of the illumination light source, and the temperature characteristics of the illumination light source.

6. The information processing apparatus according to claim 1, wherein the CPU is further configured to correct the brightness of the first image at the time of photographing operation based on the first temperature of the illumination light source at the time of photographing operation, the brightness of the first image at the time of photographing operation, and a change rate of the temperature characteristics of the illumination light source.

7. The information processing apparatus according to claim 1, wherein the CPU is further configured to calculate an amount of melanin included in a subject based on a corrected first image,
wherein the corrected first image is the first image after the brightness correction.

8. The information processing apparatus according to claim 7, wherein the CPU is further configured to calculate the amount of melanin based on a first average value of the corrected first image under a red light source and a second average value of the corrected first image under a near-infrared light source.

9. The information processing apparatus according to claim 1, wherein the CPU is further configured to calculate an amount of redness included in a subject based on a corrected first image;
wherein the corrected first image is the first image after the brightness correction.

10. The information processing apparatus according to claim 9, wherein the CPU is further configured to calculate the amount of redness based on a first average value of the corrected first image under a red light source and a second average value of the corrected first image under a green light source.

11. The information processing apparatus according to claim 1, wherein CPU is further configured to correct the first image at the time of photographing operation such that a contrast of a distribution of melanin in the first image at the time of photographing operation is emphasized.

12. The information processing apparatus according to claim 11, wherein the CPU is further configured to calculate the distribution of melanin in the first image at the time of photographing operation.

13. The information processing apparatus according to claim 1, wherein the CPU is further configured to correct the first image at the time of photographing operation such that a contrast of a distribution of an amount of redness in the first image at the time of photographing operation is emphasized.

14. The information processing apparatus according to claim 13, wherein the CPU is further configured to calculate the distribution of the amount of redness in the first image at the time of photographing operation.

15. The information processing apparatus according to claim 1, wherein the CPU is further configured to correct the exposure time period of the image capturing apparatus.

16. An information processing method, comprising:
  acquiring, by a Central Processing Unit (CPU), a first image photographed by an image capturing apparatus at a time of photographing operation;
  acquiring, by the CPU, a first temperature of an illumination light source at the time of photographing operation; and
  correcting, by the CPU, one of a brightness of the first image at the time of photographing operation or an exposure time period of the image capturing apparatus, based on the first temperature of the illumination light source at the time of photographing operation, the brightness of the first image at the time of photographing operation, a second temperature of the illumination light source at a time of calibration, a brightness of a reference image at the time of calibration, and temperature characteristics of the illumination light source,
    wherein the reference image is an image of a reference material photographed by the image capturing apparatus at the time of calibration, and
    wherein the temperature characteristics of the illuminating light source are pre-set.

17. A non-transitory computer readable medium having stored thereon, computer-executable instructions causing a computer to execute operations, the operations comprising:
  acquiring a first image photographed by an image capturing apparatus at a time of photographing operation;
  acquiring a first temperature of an illumination light source at the time of photographing operation; and
  correcting, one of a brightness of the first image at the time of photographing operation or an exposure time period of the image capturing apparatus, based on the first temperature of the illumination light source at the time of photographing operation, the brightness of the first image at the time of photographing operation, a second temperature of the illumination light source at a time of calibration, a brightness of a reference image at the time of calibration, and temperature characteristics of the illumination light source,
    wherein the reference image is an image of a reference material photographed by the image capturing apparatus at the time of calibration, and
    wherein the temperature characteristics of the illuminating light source are pre-set.

* * * * *